(12) United States Patent
Mays

(10) Patent No.: US 9,937,208 B2
(45) Date of Patent: Apr. 10, 2018

(54) MODULATION OF SPLENOCYTES IN CELL THERAPY

(75) Inventor: Robert W. Mays, Shaker Heights, OH (US)

(73) Assignee: ABT Holding Company, Cleveland, OH (US)

( * ) Notice: Subject to any disclaimer, the term of this patent is extended or adjusted under 35 U.S.C. 154(b) by 618 days.

(21) Appl. No.: 13/150,491

(22) Filed: Jun. 1, 2011

(65) Prior Publication Data

US 2011/0293642 A1 Dec. 1, 2011

Related U.S. Application Data

(63) Continuation of application No. PCT/US2011/036235, filed on May 12, 2011.

(60) Provisional application No. 61/334,001, filed on May 12, 2010, provisional application No. 61/440,617, filed on Feb. 8, 2011.

(51) Int. Cl.
| | |
|---|---|
| *A61K 38/00* | (2006.01) |
| *C12N 5/00* | (2006.01) |
| *A61K 35/28* | (2015.01) |
| *A61K 35/545* | (2015.01) |
| *C12N 5/074* | (2010.01) |
| *G01N 33/50* | (2006.01) |
| *G01N 33/68* | (2006.01) |

(52) U.S. Cl.
CPC ............ *A61K 35/28* (2013.01); *A61K 35/545* (2013.01); *C12N 5/0607* (2013.01); *G01N 33/505* (2013.01); *G01N 33/5047* (2013.01); *G01N 33/6893* (2013.01); *G01N 2333/545* (2013.01); *G01N 2333/5406* (2013.01); *G01N 2333/5412* (2013.01); *G01N 2333/5428* (2013.01); *G01N 2333/70514* (2013.01); *G01N 2333/70517* (2013.01); *G01N 2500/00* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 5,827,735 A | 10/1998 | Young et al. | |
| 5,906,934 A | 5/1999 | Grande et al. | |
| 6,090,625 A | 7/2000 | Abuljadayel | |
| 6,214,369 B1 | 4/2001 | Grande et al. | |
| 6,281,012 B1 | 8/2001 | McIntosh | |
| 6,328,960 B1 | 12/2001 | McIntosh | |
| 6,368,636 B1 | 4/2002 | McIntosh | |
| 6,387,369 B1 | 5/2002 | Pittenger et al. | |
| 6,653,134 B2 | 11/2003 | Prockop et al. | |
| 6,685,936 B2 | 2/2004 | McIntosh | |
| 6,777,231 B1 | 8/2004 | Katz et al. | |
| 6,797,269 B2 | 9/2004 | Mosca | |
| 6,875,430 B2 | 4/2005 | McIntosh | |
| 7,015,037 B1 * | 3/2006 | Furcht et al. | 435/372 |
| 7,045,148 B2 | 5/2006 | Hariri | |
| 7,056,738 B2 | 6/2006 | Prockop et al. | |
| 7,229,827 B2 | 6/2007 | Kim et al. | |
| 7,311,905 B2 | 12/2007 | Hariri | |
| 7,491,388 B1 | 2/2009 | McIntosh | |
| 7,659,118 B2 | 2/2010 | Furcht et al. | |
| 7,838,289 B2 | 11/2010 | Furcht et al. | |
| 7,883,892 B2 | 2/2011 | Verfaillie et al. | |
| 7,927,587 B2 | 4/2011 | Blazer et al. | |
| 8,075,881 B2 * | 12/2011 | Verfaillie et al. | 424/93.7 |
| 8,147,824 B2 * | 4/2012 | Maziarz et al. | 424/93.7 |
| 8,147,826 B2 * | 4/2012 | Fantuzzi | 424/94.1 |
| 8,192,348 B2 | 6/2012 | Tranquillo et al. | |
| 8,252,280 B1 | 8/2012 | Furcht et al. | |
| 8,268,619 B2 | 9/2012 | Giacomello et al. | |
| 2001/0033834 A1 | 10/2001 | Wilkison et al. | |
| 2001/0046489 A1 | 11/2001 | Habener et al. | |
| 2002/0061587 A1 | 5/2002 | Anversa | |
| 2002/0164794 A1 | 11/2002 | Wernet | |

(Continued)

FOREIGN PATENT DOCUMENTS

| | | |
|---|---|---|
| EP | 2 539 436 A1 | 1/2013 |
| EP | 2 539 439 A1 | 1/2013 |

(Continued)

OTHER PUBLICATIONS

Experimental Hematology, 2009, v.37 pp. 1445-1453.*
Yang et al ( China J of Hematology, 2008).*
Office Action and Notice of References Cited (PTO form 892) from U.S. Appl. No. 13/301,186.
Kolf, C.M., et al. Review Mesenchymal stromal cells: Biology of adult mesenchymal stem cells: regulation of niche, self-renewal and differentiation. Arthritis Research & Therapy, (2007) vol. 9:204 pp. 1-10.
Notices of References Cited (PTO form 892) from U.S. Appl. No. 13/150,491, dated Nov. 7, 2012 and Jul. 31, 2013.
Liedtke, S., et al. Oct4 expression revisited; potential pitfalls for data misinterpretation in stem cell research. Biol. Chem., (2008) vol. 389, pp. 845-850.

(Continued)

*Primary Examiner* — Michail A Belyavskyi
(74) *Attorney, Agent, or Firm* — Tarolli, Sundheim, Covell & Tummino LLP

(57) ABSTRACT

The invention provides methods for treating pathological conditions associated with an undesirable inflammatory component. The invention is generally directed to reducing inflammation by administering cells that have one or more of the following effects in an injured subject: interact with splenocytes, preserve splenic mass, increase proliferation of CD4$^+$ and CD8$^+$ T-cells, increase IL-4 and IL-10, decrease IL-6 and IL-1β, and increase M2:M1 macrophage ratio at the site of injury. The invention is also directed to drug discovery methods to screen for agents that modulate the ability of the cells to have these effects. The invention is also directed to cell banks that can be used to provide cells for administration to a subject, the banks comprising cells having desired potency for achieving these effects.

10 Claims, 22 Drawing Sheets

(56) References Cited

U.S. PATENT DOCUMENTS

| | | |
|---|---|---|
| 2003/0003090 A1 | 1/2003 | Prockop et al. |
| 2003/0032179 A1 | 2/2003 | Hariri |
| 2003/0059414 A1 | 3/2003 | Ho et al. |
| 2004/0033214 A1 | 2/2004 | Young et al. |
| 2004/0235165 A1 | 11/2004 | Prockop et al. |
| 2005/0074435 A1 | 4/2005 | Casper et al. |
| 2005/0169896 A1 | 8/2005 | Li et al. |
| 2005/0181502 A1 | 8/2005 | Furcht et al. |
| 2005/0239897 A1 | 10/2005 | Pittenger |
| 2005/0255588 A1 | 11/2005 | Young et al. |
| 2006/0008450 A1 | 1/2006 | Verfaillie et al. |
| 2006/0159666 A1 | 7/2006 | Willing et al. |
| 2006/0177925 A1 | 8/2006 | Rosenberg et al. |
| 2006/0263337 A1 | 11/2006 | Maziarz et al. |
| 2007/0059823 A1 | 3/2007 | Verfaillie et al. |
| 2008/0095749 A1 | 4/2008 | Aggarwal |
| 2008/0194024 A1 | 8/2008 | Mays |
| 2008/0213227 A1 | 9/2008 | Aggarwal |
| 2008/0274088 A1 | 11/2008 | Panoskaltsis-Mortari et al. |
| 2008/0311084 A1 | 12/2008 | Verfaillie et al. |
| 2008/0317740 A1 | 12/2008 | Blazar et al. |
| 2009/0092586 A1 | 4/2009 | Verfaillie et al. |
| 2009/0104159 A1 | 4/2009 | Prosper et al. |
| 2009/0104163 A1 | 4/2009 | Deans et al. |
| 2009/0203128 A1 | 8/2009 | Giger |
| 2009/0203130 A1 | 8/2009 | Furcht et al. |
| 2009/0233353 A1 | 9/2009 | Furcht et al. |
| 2009/0233354 A1 | 9/2009 | Furcht et al. |
| 2010/0008890 A1 | 1/2010 | Mays et al. |
| 2010/0150876 A1 | 6/2010 | Verfaillie et al. |
| 2010/0172885 A1 | 7/2010 | Pittenger |
| 2010/0239542 A1 | 9/2010 | Young et al. |
| 2010/0239543 A1 | 9/2010 | Young et al. |
| 2010/0285590 A1 | 11/2010 | Verfaillie et al. |
| 2010/0310570 A1 | 12/2010 | Mays et al. |
| 2011/0020292 A1 | 1/2011 | Van't Hof |
| 2011/0020293 A1 | 1/2011 | Woda et al. |
| 2011/0027238 A1 | 2/2011 | Aggarwal |
| 2011/0064701 A1 | 3/2011 | Young et al. |
| 2011/0111492 A1 | 5/2011 | Hu et al. |
| 2011/0171659 A1 | 7/2011 | Furcht et al. |
| 2011/0177595 A1 | 7/2011 | Furcht et al. |
| 2011/0206647 A1 | 8/2011 | Woda et al. |
| 2011/0212069 A1 | 9/2011 | Hamilton et al. |
| 2011/0243901 A1 | 10/2011 | Blazar et al. |
| 2011/0287539 A1 | 11/2011 | Pauwelyn et al. |
| 2011/0293578 A1 | 12/2011 | Busch et al. |
| 2011/0305638 A1* | 12/2011 | Ting et al. ............ 424/9.1 |
| 2011/0311496 A1 | 12/2011 | Pittenger |
| 2011/0318313 A1* | 12/2011 | Cox et al. ............ 424/93.7 |
| 2011/0318314 A1 | 12/2011 | Aggarwal |
| 2011/0318315 A1 | 12/2011 | Aggarwal |
| 2012/0009672 A1 | 1/2012 | Sancho-Bru et al. |
| 2012/0009674 A1 | 1/2012 | Mays |
| 2012/0021019 A1 | 1/2012 | Giacomello et al. |
| 2012/0052568 A1 | 3/2012 | Subramanian et al. |
| 2012/0064047 A1 | 3/2012 | Verfaillie et al. |
| 2012/0182103 A1 | 7/2012 | Miyabara |
| 2012/0308531 A1 | 12/2012 | Pinxteren et al. |
| 2016/0069903 A1* | 3/2016 | Lakadamyali ..... G01N 33/6875 435/7.1 |

FOREIGN PATENT DOCUMENTS

| | | |
|---|---|---|
| WO | WO 96/23870 | 8/1996 |
| WO | WO 99/16863 | 4/1999 |
| WO | WO 99/35243 | 7/1999 |
| WO | WO 01/04268 | 1/2001 |
| WO | 200111011 A2 | 2/2001 |
| WO | WO 01/08691 | 2/2001 |
| WO | WO 01/21766 | 3/2001 |
| WO | WO 01/21767 | 3/2001 |
| WO | WO 02/08388 | 3/2001 |
| WO | WO 01/62901 | 8/2001 |
| WO | WO 02/34890 | 5/2002 |
| WO | 2008020666 A1 | 2/2008 |
| WO | 2009007852 A2 | 1/2009 |
| WO | 2009092092 A1 | 7/2009 |
| WO | 2009136283 A2 | 11/2009 |
| WO | 2011106476 A1 | 9/2011 |

OTHER PUBLICATIONS

Atlasi, Y., et al. Oct4 Spliced Variants are Differentially Expressed in Human Pluripotent and Nonpluripotent Cells. Stem Cells, (2008) vol. 26, pp. 3068-3074.

Moriscot, C., et al. Human bone marrow mesenchymal stem cells can express insulin and key transcription factors of the endocrine pancreas developmental pathway upon genetic and/or micro-environmental manipulation in vitro. Stem Cells, (2005) vol. 23, pp. 594-603.

Roche, S., et al. Oct-4, Rex-1, and Gata-4 expression in human MSC increase the differentiation efficiency but not hTERT expression. J. Cell, Biochem. (2007) vol. 101, pp. 271-280.

Tai, M.H., et al. Oct4 expression in adult human stem cells: evidence in support of the stem cell theory of carcinogenesis. Carcinogenesis (2005) vol. 26, pp. 495-502.

Tondreau, T., et al. Mesenchymal stem cells derived from CD133-positive cells in mobilized peripheral blood and cord blood: proliferation, Oct4 expression, and plasticity. Stem Cells (2005) vol. 23, pp. 1105-1112.

Takeda, J., et al. Human Oct3 gene family: cDNA sequences, alternative splicing, gene organization chromosomal location, and expression at low levels in adult tissues. Nucleic Acids Research (1992) vol. 20, No. 17, pp. 4613-4620.

Brehm, A., et al. The Carboxy-Terminal Transactivation Domain of Oct-4 Acquires Cell Specificity through the POU Domain. Mol. Cell. Biol. (1997) vol. 17, No. 1, pp. 154-162.

Jiang, Y., et al. Pluripotency of mesenchymal stem cells derived from adult marrow. Nature (2002) vol. 418, pp. 41-49.

Mahmood, A., et al. Treatment of Traumatic Brain Injury in Adult Rats with Intravenous Administration of Human Bone Marrow Stromal Cells. Neurosurgery (2003) vol. 53, pp. 697-703.

Woodbury, D., et al. Adult Rat and Human Bone Marrow Stromal Cells Differentiate Into Neurons. J of Neuroscience Research (2000), vol. 61, pp. 364-370.

Digirolamo, C.M., et al. Propagation and senescence of human marrow stromal cells in culture: a simple colony-forming assay identifies samples with the greatest potential to propagate and differentiate. British Journal of Haematology (1999) vol. 107, pp. 275-281.

Ohtaki, H., et al. Stem/progenitor cells from bone marrow decrease neuronal death in global ischemia by modulation of inflammatory/immune responses. PNAS (2008) vol. 105, No. 38, pp. 14638-14543.

Cambrex specimens, "Poietics Human Mesenchymal Stem Cell Systems," Cambrex BioScience Walkersville, Inc. (2005).

Prockop, D., "Marrow stromal cells as stem cells for nonhematopoietic tissues" Science; 276:71-74 (1997).

Bjornson et al., "Turning brain into blood: a hematopoietic fate adopted by adult neural stem cells in vivo" Science; 283:534-537 (1999).

Reyes et al., "Purification and ex vivo expansion of postnatal human marrow mesodermal progenitor cells" Blood; 98:2615-25 (2001).

Bouwens, L., "Transdifferentiation versus stem cell hypothesis for the regeneration of islet beta-cells in the pancreas" Microscopy Research and Technique; 43:332-336 (1998).

Reyes et al., "Origin of endothelial progenitors in human postnatal bone marrow" J. Clin. Invest.; 109:1-10 (2002).

Reyes et al., "Characterization of multilineage mesodermal progenitor cells in adult marrow" Abstract No. 124, American Society for Hematology (2001).

Reyes et al., "Turning marrow into brain: generation of glial and neuronal cells from adult bone marrow mesenchymal stem cells" Abstract No. 1676, American Society for Hematology (2001).

(56) References Cited

OTHER PUBLICATIONS

Reyes et al., "Skeletal smooth and cardiac muscle differentiation from single adult marrow derived mesodermal progenitor cells" Abstract No. 2610, American Society for Hematology (2001).
Reyes et al., "In vitro and in vivo characterization of neural cells derived from mesenchymal stem cells" Abstract 2126, American Society for Hematology (2001).
Reyes et al., "Endothelial cells generated from human marrow derived mesenchymal stem cells (MSC)" Abstract No. 2276, American Society for Hematology (2001).
Zhao et al., "Immunohistochemical identification of multipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291-1302 (2002).
Zhao et al., "Human bone marrow stem cells exhibit neural phenotypes and ameliorate neurological deficits after grafting into the ischemic brain of rats" Exp Neurol; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi al., "Identification of genes responsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002).
Verfaille, C., "Optimizing hematopoietic stem cell engraftment: a novel role for thrombopoeitin" J. Clin. Invest.; 110:303-304 (2002).
Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol.; 30:582-589 (2002).
Lewis et al., "Multi-lineage expansion potential of primitive hematopoietic progenitors: superiority of umbilical cord blood compared to mobilized peripheral blood" Exp. Hematol.; 28:1087-1095 (2002).
Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).
Punzel et al., "The myeloid-lymphoid initiating cell (ML-IC) assay assesses the fate of multipotent human progenitors in vitro" Blood; 93:3750-3756 (1999).
Roy et al "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin−/DR-cells in stroma-derived soluble factors, interleukin-3, and macrophage inflammatory protein-1 alpha maintains not only myeloid but also lymphoid progenitors in a novel switch culture assay" Blood; 15:4516-4522 (1998).
Verfaillie, C., "Stem cells in chronic myelogenous Leukemia" Hematol. Oncol. Clin. North Am.; 11:1079-1114 (1997).
Prosper et al., "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).

Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientists herald a versatile adult cell" The New York Times on the Web, Jan. 25, 2002.
Rosford et al., "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mol. Cell Biol.; 18:1866-1878 (1998).
Reyes et al., "Characterization of multipotent adult progenitor cells, a subpopulation of mesenchymal stem cells" Annals of the New York Academy of Science; 938:231-235 (2001).
Anjos-Afonso and Bonnet, "Nonhematopoietic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.; 118:3925-36 (2005).
Bodnar et al., "Extension of life-span by introduction of telomerase into normal human cells" Science; 279:349-352 (1998).
Horwitz et al., "Clarification of the nomenclature for MSC: the international society for cellular therapy position paper" Cytotherapy; 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype" J Neurosci Res; 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stem cells" Leukemia; 17:1146-1149 (2003).
Izadpanah et al., "Biologic properties of mesenchymal stem cells derived from bone marrow and adipose tissue" Journal of Cellular Biochemistry; 99:1285-1297 (2006).
Long et al., "Neural cell differentiation in vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or macroenvironmental manipulation in vitro" Stem Cells; 23:594-604 (2005).
Sanchez-Ramos et al., "Adult bone marrow stromal cells differentiate into neural cells in vitro" Exp. Neurol.; 164:247-56 (2000).
Eglitis et al., "Hematopoietic cells differentiate into both microglia and macroglia in the brain of adult mice" Proc. Natl. Acad. Sci. USA; 94:4080-85 (1997).
Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).
Lagasse et al., "Purified hematopoietic stem cells can differentiate into hepatocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).

(56) References Cited

OTHER PUBLICATIONS

Aldhous et al., "Fresh questions on stem cell findings" New Scientist, Mar. 21, 2007.
Brazelton et al., "From marrow to brain: expression of neuronal phenotypes in adult mice" Science; 290:1775-9 (2000).
Clarke et al., "Generalized potential of adult neural stem cells" Science; 288: 1660-3 (2000).
Johansson et al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).
Morshead et al., "Hematopoletic competence is a rare property of neural stem cells that may depend on genetic and epigenetic alterations" Nat. Med.; 8:268-73 (2002).
Petersen et al., "Bone marrow as a potential source of hepatic oval cells" Science; 284:1168-70 (1999).
Scintu et al., "Differentiation of human bone marrow stem cells into cells with a neural phenotype: diverse effects of two specific treatments" BMC Neurosci.; 7:14 (2006).
U.S. Patent and Trademark Office, Office Action dated Jun. 24, 2005 in related U.S. Appl. No. 10/040,757.
U.S. Patent and Trademark Office, Office Action and 892 dated Jun. 27, 2008 in related U.S. Appl. No. 10/467,963.
U.S. Patent and Trademark Office, Office Action dated Oct. 15, 2009 in related U.S. Appl. No. 10/467,963.
U.S. Patent and Trademark Office, Office Action and 892 dated Apr. 7, 2008 in related U.S. Appl. No. 11/151,689.
U.S. Patent and Trademark Office, Office Action dated Jan. 4, 2006 in related U.S. Appl. No. 11/238,234.
U.S. Patent and Trademark Office, Office Action dated Aug. 29, 2006 in related U.S. Appl. No. 11/238,234.
Vendrame et al., "Cord blood rescues stroke-induced changes in splenocyte phenotype and function" Experimental Neurology; 199(1):191-200 (2006).
Xioa et al., "Transplantation of a novel cell line population of umbilical cord blood stem cells ameliorates neurological deficits associated with ischemic brain injury," Stem Cells and Development; 14(6):722-733 (2005).
Walker et al., "Progenitor cell therapies for traumatic brain injury; barriers and opportunities in translation" Disease Models & Mechanisms 2:(1-2):23-38, (Feb. 31, 2009).
U.S. Patent and Trademark Office, Office Action and 892 dated Apr. 3, 2007 in related U.S. Appl. No. 11/238,234.
U.S. Patent and Trademark Office, Office Action dated Oct. 7, 2008 in related U.S. Appl. No. 11/238,234.
Communication and 1449, filed Oct. 2, 2007 in related U.S. Appl. No. 11/238,234, and supplemental 1449 submitted on Oct. 4, 2007.
Information Disclosure Statement, Second Communication and PTO/SB/08b, filed Dec. 24, 2008 in related U.S. Appl. No. 11/238,234.
International Search Report for PCT/US2011/36235; dated Aug. 9, 2011.
Mays, R.W., et al. Development of adult pluripotent stem cell therapies for ischemic injury and disease. Expert Opinion on Biological Therapy; ( 2007) vol. 7, No. 2; pp. 173-184.
Walker, P.A., et al. Intravenous multipotent adult progenitor cell therapy for traumatic brain injury: Preserving the blood brain barrier via an interaction with splenocytes. Exp Neurology; (2010) vol. 225, No. 2; pp. 341-352.
Walker, P.A., et al. Intravenous multipotent adult progenitor cell therapy after traumatic brain injury: modulation of the resident microglia population. J Neuroinflammation; (2012) vol. 9, No. 1; pp. 228-241.
Extended European Search Report for corresponding application No. EP11781272; dated Oct. 7, 2013.
Gendron, A, et al., 'Temporal affects of left versus right middle cerebral artery occlusion on spleen lymphocyte subsets and mitogenic response in Wistar rats,' Brain Research, 2002, vol. 955, pp. 85-97.
Benner, E.J. et al., 'Therapeutic immunization protects dopaminergic neurons in a mouse model of Parkinson's disease,' Proc Natl Acad Sci USA, 2004, vol. 101, pp. 9435-9440.
Boozer et al., "Global Characterization and Genomic Stability of Human MultiStem, A Multipotent Adult Progenitor Cell," J Stem Cells., 4(1), pp. 17-28, 2009.
U.S. Appl. No. 11/808,933, filed Jun. 13, 2007, High Oct3/4 MAPCs and Methods Therefor.
U.S. Appl. No. 13/510,491, filed May 17, 2012, Reducing Inflammation Using Cell Therapy.
U.S. Appl. No. 13/071,801, filed Mar. 25, 2011, Modulation of Macrophahe Activation.

* cited by examiner

Anti-inflammatory cytokines must act through other effector cells.

M1-Classical Activation; M2-Alternative Activation

Cytokine and lymphocyte output drives macrophage phenotype.

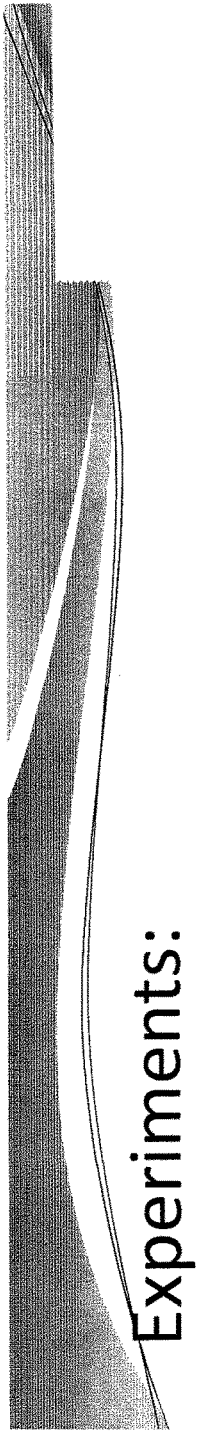

Experiments:

- Animals: Long-Evans Rats, Male, 300-320g
- Ischemic Stroke Model: CCAo/MCAo for 3 hrs
- Cells dosing and route: $1.2 \times 10^7$/kg, iv
- Timing: Cell/saline infusion at 24 hours after Stroke
- Behavior test: Cylinder test
- Endpoints:
  - Behavioral tests up to 28 days post-MCAo
  - Lesion size measurements at 28 days post-MCAo
  - Serum cytokines measured 3 days post-treatment
  - Spleen mass measured at 3 days post-treatment
  - IL-10 gene level changes by microarray at 3 days post-treatment

Figure 16

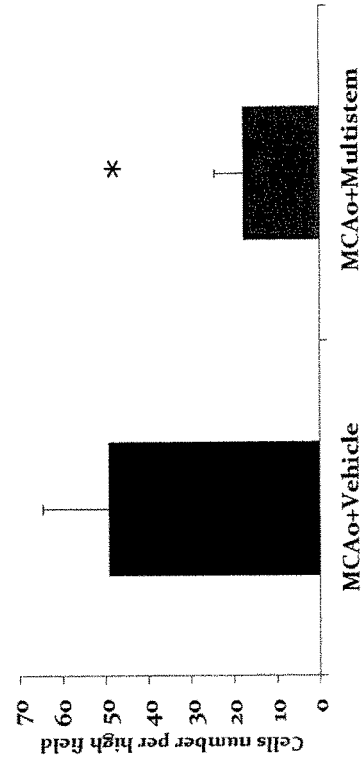
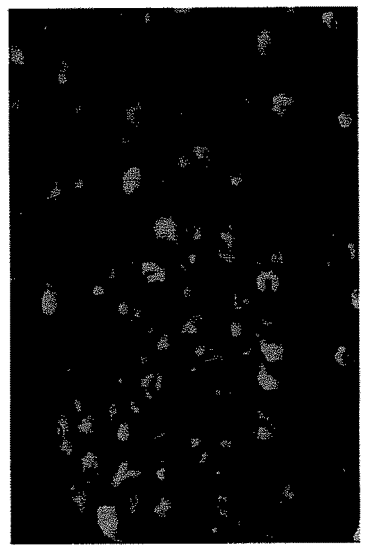
Figure 21

MODULATION OF SPLENOCYTES IN CELL THERAPY

This application claims priority to U.S. Application No. 61/440,617, filed Feb. 8, 2011; U.S. Application No. 61/334, 001, filed May 12, 2010; and PCT/US2011/036235, filed May 12, 2011 which are all incorporated by reference.

FIELD OF THE INVENTION

The invention provides methods for treating conditions associated with an undesirable inflammatory component, e.g., conditions of the central nervous system (CNS). The invention is generally directed to reducing inflammation at a site of injury by administering cells that interact with splenocytes in the spleen to affect proliferation and/or activation of the splenocytes and increase systemic levels of anti-inflammatory cytokines that cause an effect at the site of the injury (i.e., have an endocrine effect). The end result may be to increase the relative numbers of M2 macrophages (alternate activated/anti-inflammatory) relative to M1 macrophages (classically activated/pro-inflammatory). The invention is also directed to drug discovery methods to screen for agents that modulate the ability of the administered cells to achieve these effects. The invention is also directed to cell banks that can be used to provide cells for administration to a subject, the banks comprising cells having a desired potency for achieving these effects. The invention is also directed to compositions comprising cells of specific potency for achieving these effects, such as pharmaceutical compositions. The invention is also directed to methods for evaluating the dose efficacy of the cells to achieve these effects in a patient by assessing the in vivo or in vitro effects. The invention is also directed to diagnostic methods conducted prior to administering the cells to a subject to be treated, including assays to assess the desired potency of the cells to be administered. The invention is further directed to post-administration diagnostic assays to assess the effect of the cells on a subject being treated and adjust the dosage regimen. These assays can be performed on an ongoing basis along with treatment. The cells are non-embryonic stem, non-germ cells that can be characterized by one or more of the following: extended replication in culture and express markers of extended replication, such as telomerase, express markers of pluripotentiality, and have broad differentiation potential, without being transformed.

SUMMARY OF THE INVENTION

Loss of splenic mass/immune effector cells following injury, e.g., CNS injury, also leads to decreased immunocompetence in a subject. Accordingly, opportunistic infection often complicates recovery. Discovery of a method to preserve immune competence, therefore, would promote more complete post-injury recovery.

The inventors have found that certain cells have an immunomodulatory effect on an injury without being in geographical proximity to that injury, i.e., have a systemic effect. These cells, when administered intravenously, interact with splenocytes in the spleen and the interaction of these cells with splenocytes in spleen results in the systemic presence of anti-inflammatory cytokines. Without being bound to a particular mechanism, the cytokines may act to alter the ratio of M1/M2 macrophages at the site of injury so that the ratio of M2/M1 macrophages increases. This leads to increased anti-inflammatory effects.

In fact, in a model of traumatic brain injury, the number of M2 macrophages at the site of injury was greatly increased when cells described herein were administered intravenously to an injured subject (Example 2 in this application).

Accordingly, there are several effects associated with the interaction of the cells with splenocytes in the spleen. One of these is to preserve splenic mass. Normally, injury or trauma is associated with an exit of lymphocytes from the spleen and apoptosis of some cell types in the spleen that results in a concomitant decrease in splenic mass. Interaction of the cells with splenocytes in the spleen results in an increase in splenocyte proliferation. Interaction of the cells with splenocytes in the spleen results in higher $CD4^+$ T-cells principally composed of T-regulatory cells ($CD4^+$, $FoxP3^+$ immunophenotype) in the spleen. Interactions of the cells with the spleen also results in a decreased apoptotic index of cells in the spleen. Accordingly, interaction of the cells with splenocytes reduces or prevents this loss of splenic mass. There is also increased production of anti-inflammatory cytokines, such as IL-4 and IL-10. One result of the increase in production in anti-inflammatory cytokines is a decrease in the M1:M2 ratio of macrophages at the site of injury.

Because interaction of the cells with splenocytes causes the effects, the cells can be administered systemically instead of locally, including for conditions where systemic administration would have been expected to be ineffective. This includes conditions involving the central nervous system (CNS), where the blood/brain barrier would have been expected to prevent any paracrine effects of the cells on the injury site.

Because the effect of the interaction can be easily measured, e.g., by splenic mass, T-cell numbers and ratios, cytokine expression, and macrophage activation state, the invention provides a real-time diagnostic marker to assess the efficacy of and adjust the dosage regimen of the cells.

Because the interaction produces measurable/detectable effects, its occurrence can be assessed in any injury or condition. If it does occur in a given injury or condition, treatment and therapeutic regimen can, accordingly, be tailored.

Because in vitro and in vivo assays exist to measure a cell's ability to interact with splenocytes and produce the desired effects, cells can be identified and banked for future off-the-shelf use.

Because the effects of interaction occur within a short time frame after injury, this provides a defined window of time to begin treatment.

Accordingly, the invention covers various embodiments.

The invention is broadly directed to methods for modulating the M1:M2 macrophage activation at a site of injury.

The invention is also directed to improving immune competence in a subject following an insult that leads to reduced proliferation of splenocytes in spleen, e.g., reduction in $CD4^+$ and $CD8^+$ T-cell production in spleen.

The invention is more specifically directed to CNS injury and methods for reducing macrophage neurotoxic activation and/or increasing macrophage neuroprotective activation in CNS conditions.

Macrophages secrete the cytokines IL-1β, IL-6, IL-12, TNFα, CXCL8 (IL-8), TWEAK, GMCSF, IL-1-α, IL-IRA, IL-27, and OSM (oncostatin M). Macrophages secrete the chemokines CXCL8, CCL4 (MIP 1-β), CCL2 (MCP-1), and CX3CL1.

Factors that induce neuroprotective activation include, but are not limited to, CCL21 and CXCL10. Factors that suppress neurotoxic activation include, but are not limited to, TGFβ, CCL5, NGF, Galectin-1, Pentraxin-3, VEGF, BDNF, HGF, adrenomedullin, and thrombospondin.

Factors expressed and/or secreted by macrophages during activation include, but are not limited to, iNOS, CD16, CD86, CD64, and CD32, scavenger receptor A, CD163, arginase 1, CD14, CD206, CD23, and scavenger receptor B, TNF receptors, CD40 receptor, $O_2^-$, NO, B7 molecules, MHCII, and IL-18 (IGIF).

Factors secreted by macrophages during neurotoxic activation include, but are not limited to, iNOS, CD16, CD86, CD64, and CD32. Factors secreted by macrophages during neuroprotective activation include, but are not limited to, scavenger receptor A, CD163, arginase 1, CD14, CD206, CD23, and scavenger receptor B.

The invention is also directed to methods for reducing injury, including, but not limited to, acute and chronic conditions in cardiovascular, e.g., acute myocardial infarction; peripheral vascular disease; pulmonary, e.g., asthma, ARDS; autoimmune, e.g., rheumatoid arthritis, multiple sclerosis, lupus, scleroderma; psoriasis; gastrointestinal, e.g., graft-versus-host-disease, Crohn's disease, diabetes, ulcerative colitis, acute and chronic transplantation rejection, colitis, alveolitis, bronchiolitis obliterans, ileitis, pancreatitis, glomerulonephritis, uveitis, arthritis, hepatitis, dermatitis, and enteritis.

The invention is also directed to methods for reducing CNS injury, including, but not limited to, ischemic stroke, multiple sclerosis, Alzheimer's Disease, ALS, Parkinson's Disease, hypoxic-ischemia, neonatal hypoxic ischemia, and traumatic brain or spinal cord injury.

The above methods are carried out by administering certain cells to a subject. Cells include, but are not limited to, cells that are not embryonic stem cells and not germ cells, having some characteristics of embryonic stem cells, but being derived from non-embryonic tissue, and providing the effects described in this application. The cells may naturally achieve these effects (i.e., not genetically or pharmaceutically modified). However, natural expressors can be genetically or pharmaceutically modified to increase potency.

The cells may express pluripotency markers, such as oct4. They may also express markers associated with extended replicative capacity, such as telomerase. Other characteristics of pluripotency can include the ability to differentiate into cell types of more than one germ layer, such as two or three of ectodermal, endodermal, and mesodermal embryonic germ layers. Such cells may or may not be immortalized or transformed in culture. The cells may be highly expanded without being transformed and also maintain a normal karyotype. For example, in one embodiment, the non-embryonic stem, non-germ cells may have undergone at least 10-40 cell doublings in culture, such as 50, 60, or more, wherein the cells are not transformed and have a normal karyotype. The cells may differentiate into at least one cell type of each of two of the endodermal, ectodermal, and mesodermal embryonic lineages and may include differentiation into all three. Further, the cells may not be tumorigenic, such as not producing teratomas. If cells are transformed or tumorigenic, and it is desirable to use them for infusion, such cells may be disabled so they cannot form tumors in vivo, as by treatment that prevents cell proliferation into tumors. Such treatments are well known in the art.

Cells include, but are not limited to, the following numbered embodiments:

1. Isolated expanded non-embryonic stem, non-germ cells, the cells having undergone at least 10-40 cell doublings in culture, wherein the cells express oct4, are not transformed, and have a normal karyotype.

2. The non-embryonic stem, non-germ cells of 1 above that further express one or more of telomerase, rex-1, rox-1, or sox-2.

3. The non-embryonic stem, non-germ cells of 1 above that can differentiate into at least one cell type of at least two of the endodermal, ectodermal, and mesodermal embryonic lineages.

4. The non-embryonic stem, non-germ cells of 3 above that further express one or more of telomerase, rex-1, rox-1, or sox-2.

5. The non-embryonic stem, non-germ cells of 3 above that can differentiate into at least one cell type of each of the endodermal, ectodermal, and mesodermal embryonic lineages.

6. The non-embryonic stem, non-germ cells of 5 above that further express one or more of telomerase, rex-1, rox-1, or sox-2.

7. Isolated expanded non-embryonic stem, non-germ cells that are obtained by culture of non-embryonic, non-germ tissue, the cells having undergone at least 40 cell doublings in culture, wherein the cells are not transformed and have a normal karyotype.

8. The non-embryonic stem, non-germ cells of 7 above that express one or more of oct4, telomerase, rex-1, rox-1, or sox-2.

9. The non-embryonic stem, non-germ cells of 7 above that can differentiate into at least one cell type of at least two of the endodermal, ectodermal, and mesodermal embryonic lineages.

10. The non-embryonic stem, non-germ cells of 9 above that express one or more of oct4, telomerase, rex-1, rox-1, or sox-2.

11. The non-embryonic stem, non-germ cells of 9 above that can differentiate into at least one cell type of each of the endodermal, ectodermal, and mesodermal embryonic lineages.

12. The non-embryonic stem, non-germ cells of 11 above that express one or more of oct4, telomerase, rex-1, rox-1, or sox-2.

13. Isolated expanded non-embryonic stem, non-germ cells, the cells having undergone at least 10-40 cell doublings in culture, wherein the cells express telomerase, are not transformed, and have a normal karyotype.

14. The non-embryonic stem, non-germ cells of 13 above that further express one or more of oct4, rex-1, rox-1, or sox-2.

15. The non-embryonic stem, non-germ cells of 13 above that can differentiate into at least one cell type of at least two of the endodermal, ectodermal, and mesodermal embryonic lineages.

16. The non-embryonic stem, non-germ cells of 15 above that further express one or more of oct4, rex-1, rox-1, or sox-2.

17. The non-embryonic stem, non-germ cells of 15 above that can differentiate into at least one cell type of each of the endodermal, ectodermal, and mesodermal embryonic lineages.

18. The non-embryonic stem, non-germ cells of 17 above that further express one or more of oct4, rex-1, rox-1, or sox-2.

19. Isolated expanded non-embryonic stem, non-germ cells that can differentiate into at least one cell type of at least two of the endodermal, ectodermal, and mesodermal embryonic lineages, said cells having undergone at least 10-40 cell doublings in culture.

20. The non-embryonic stem, non-germ cells of 19 above that express one or more of oct4, telomerase, rex-1, rox-1, or sox-2.

21. The non-embryonic stem, non-germ cells of 19 above that can differentiate into at least one cell type of each of the endodermal, ectodermal, and mesodermal embryonic lineages.

22. The non-embryonic stem, non-germ cells of 21 above that express one or more of oct4, telomerase, rex-1, rox-1, or sox-2.

In one embodiment, the subject is human.

In view of the property of the cells to achieve the desired effects, the cells can be used in drug discovery methods to screen for an agent that affects the ability of the cells to achieve any of the effects. Such agents include, but are not limited to, small organic molecules, antisense nucleic acids, siRNA DNA aptamers, peptides, antibodies, non-antibody proteins, cytokines, chemokines, and chemo-attractants.

In a specific embodiment, the cells are screened for an agent that enhances the cells' ability to up-regulate IL-10 and/or IL-4 and/or down-regulate IL-6 and/or IL-1β.

In view of the property of the cells to achieve the effects, cell banks can be established containing cells that are selected for having a desired potency to achieve any of the effects. Accordingly, the invention encompasses assaying cells for the ability to, for example, interact with splenocytes, preserve splenic mass, increase splenocyte proliferation, increase the production of anti-inflammatory cytokines, increase macrophage M2:M1 ratio, increase $CD8^+$ T-cells and $CD4^+$ T-cells in the spleen, and the like. The bank can provide a source for making a pharmaceutical composition to administer to a subject. Cells can be used directly from the bank or expanded prior to use. Especially in the case that the cells are subjected to further expansion, after expansion it is desirable to validate that the cells still have the desired potency. Banks allow the "off the shelf" use of cells that are allogeneic to the subject.

Accordingly, the invention also is directed to diagnostic procedures conducted prior to administering the cells to a subject. The procedures include assessing the potency of the cells to achieve the effects described in this application. The cells may be taken from a cell bank and used directly or expanded prior to administration. In either case, the cells could be assessed for the desired potency. Especially in the case that the cells are subjected to further expansion, after expansion it is desirable to validate that the cells still have the desired potency. Or the cells can be derived from the subject and expanded prior to administration. In this case, as well, the cells could be assessed for the desired potency prior to administration back to the subject (autologous).

In a specific embodiment of the invention, the cells are banked after selection for having a desired potency for down-regulating IL-6 and/or IL-1β and/or up-regulating IL-10 and/or IL-4.

In a clinical setting, one may administer the cells after obtaining a baseline by assaying for one or more of splenic mass, $CD4^+$ T-cells, $CD8^+$ T-cells, M2 macrophages, M1 macrophages, and T-regulatory cells, either directly or by means of gene expression and, then, following administration of the cells during treatment, monitor one or more times for one or more of these effects. One could then determine the optimized dose for treatment.

In a specific embodiment, one obtains the baseline by assaying one or more of IL-10, IL-6, or IL-1β.

Accordingly, the invention also is directed to diagnostic procedures conducted prior to administering the cells to a subject, the pre-diagnostic procedures including assessing the potency of the cells to achieve one or more of the desired effects. The cells may be taken from a cell bank and used directly or expanded prior to administration. In either case, the cells would be assessed for the desired potency. Or the cells can be derived from the subject and expanded prior to administration. In this case, as well, the cells would be assessed for the desired potency prior to administration.

In a specific embodiment, the diagnostic procedure involves assessing the potency of the cells to up-regulate IL-10 and/or IL-4 and/or down-regulate IL-6 and/or IL-1β.

Although the cells selected for the effects are necessarily assayed during the selection procedure, it may be preferable and prudent to again assay the cells prior to administration to a subject for treatment to confirm that the cells still achieve the effects at desired levels. This is particularly preferable where the cells have been stored for any length of time, such as in a cell bank, where cells are most likely frozen during storage.

With respect to methods of treatment with cells that achieve the desired effects, between the original isolation of the cells and the administration to a subject, there may be multiple (i.e., sequential) assays for the effects. This is to confirm that the cells can still achieve the effects, at desired levels, after manipulations that occur within this time frame. For example, an assay may be performed after each expansion of the cells. If cells are stored in a cell bank, they may be assayed after being released from storage. If they are frozen, they may be assayed after thawing. If the cells from a cell bank are expanded, they may be assayed after expansion. Preferably, a portion of the final cell product (that is physically administered to the subject) may be assayed.

The invention further includes post-treatment diagnostic assays, following administration of the cells, to assess efficacy. The diagnostic assays include, but are not limited to, measuring splenic mass (for example, by ultrasound), measuring the amount of $CD4^+$ and $CD8^+$ T-cells (particularly $CD4^+$ T-regulatory cells and $CD8^+$ T-effector cells), measuring the level of anti-inflammatory cytokines, such as IL-4, IL-10, TGF-β, and IL-35, measuring the level of pro-inflammatory cytokines, such as TNF-α, Il-1β, IL-6, and IL-17, measuring macrophages in the M2 and/or M1 activation state (including the M1:M2 ratio), and assaying factors expressed and/or secreted by the activated macrophages. These can be derived from the patient's serum, blood, tissue, etc.

In a specific embodiment, the post-treatment diagnostic assay would be to assess the up-regulation of IL-10 and/or IL-4 and/or down-regulation of IL-6 and/or IL-1β in a subject.

The invention is also directed to a method for establishing the dosage of such cells by assessing the potency of the cells to achieve one or more of the above effects. In this case, the potency would be determined and the dosage adjusted accordingly In a specific embodiment, the cells are assessed for potency to up-regulate IL-10 and/or IL-4 and/or down-regulate IL-6 and/or IL-1β.

In this case, one would monitor efficacy, by methods including one or more of the assays described in this application, to establish and maintain a proper dosage regimen.

In a specific embodiment, an assay to monitor efficacy is to assess the up-regulation of IL-10 and/or IL-4 and/or the down-regulation of IL-6 and/or IL-1β in the subject.

The invention is also directed to compositions comprising a population of the cells having a desired potency to achieve the desired effects. Such populations may be found as pharmaceutical compositions suitable for administration to a subject and/or in cell banks from which cells can be used directly for administration to a subject or expanded prior to administration. In one embodiment, the cells have enhanced (increased) potency compared to the previous (parent) cell population. Parent cells are as defined herein. Enhancement can be by selection of natural expressors or by external factors acting on the cells.

In a specific embodiment, the cells in the composition have a desired potency to up-regulate IL-10 and/or IL-4 and/or down-regulate IL-6 and/or IL-1β.

The methods and compositions of the invention are useful for treating any disease involving inflammation. This includes, but is not limited to, acute and chronic conditions in cardiovascular, e.g., acute myocardial infarction; peripheral vascular disease; pulmonary, e.g., asthma, ARDS; autoimmune, e.g., rheumatoid arthritis, multiple sclerosis, lupus, sclerodoma; psoriasis; gastrointestinal, e.g., graft-versus-host-disease, Crohn's disease, diabetes, ulcerative colitis, acute and chronic transplantation rejection, and dermatitis.

The methods and compositions of the invention are useful for treating any CNS condition involving inflammation, including, but not limited to, ischemic stroke, multiple sclerosis, Alzheimer's Disease, ALS, Parkinson's Disease, hypoxic-ischemia, neonatal hypoxic ischemia, traumatic brain or spinal cord injury, and lysosomal storage disorders.

In one particular embodiment, the methods and compositions of the invention are used in the context of hypoxic ischemia (stroke). For these treatments, one would administer the cells that achieve the effects described in this application. Such cells could have been assessed for the potency and selected for desired potency.

It is understood, however, that for treatment of any of the above conditions, it may be expedient to use such cells; that is, one that has been assessed for achieving the desired effects and selected for a desired level of efficacy prior to administration for treatment of the condition.

In all of the above assays for IL-10, IL-4, IL-6 and IL-1β, up- and down-regulation can be in the context of regulating the expression of these molecules in vivo, such as in a disease context, for example, stroke. Or regulating the expression of these molecules can be in an in vitro context, such as regulating expression of these molecules produced in other cell types that are exposed to the cells of the invention, or to medium conditioned by the cells of the invention, or extracts of such conditioned medium In a highly specific embodiment, the pathology is traumatic brain injury, spinal cord injury, or stroke and the cells are non-embryonic, non-germ cells that express pluripotentiality markers, e.g., one or more of telomerase, rex-1, sox-2, oct4, rox-1, nanog, SSEA-1, and SSEA-4, and/or have broad differentiation potential, e.g., at least two of ectodermal, endodermal, and mesodermal cell types. Here, intravenous administration is preferred.

The cells may be prepared by the isolation and culture conditions described herein. In a specific embodiment, they are prepared by culture conditions that are described herein involving lower oxygen concentrations combined with higher serum, such as those used to prepare the cells designated "MultiStem®."

BRIEF DESCRIPTION OF THE FIGURES

FIG. 16—This figure shows various parameters for conducting the experiments shown in the following FIGS. 17-22).

FIG. 21—TUNEL positive cells in treated versus control animals. There are less TUNEL positive cells found in MultiStem® treated animals versus vehicle-treated animals after MCAo.

DETAILED DESCRIPTION OF THE INVENTION

Figure 1:
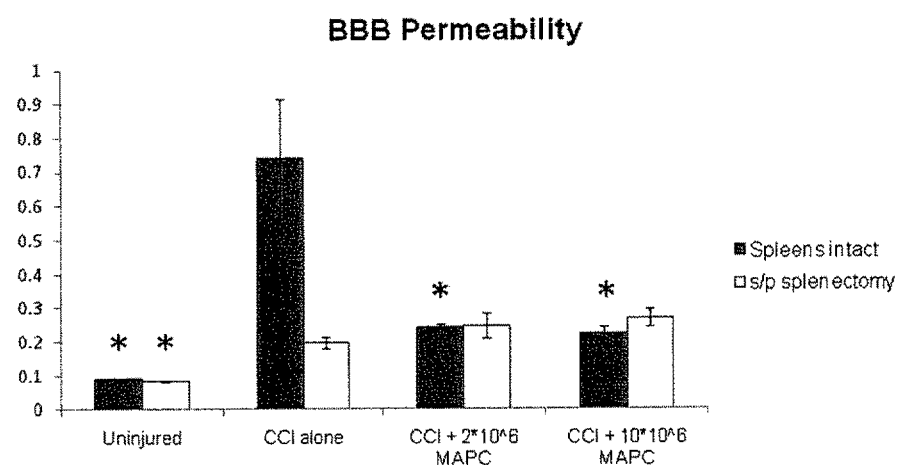
FIG. 1—Blood brain barrier (BBB) permeability measured via Evan's blue extravasation. BBB permeability measurement (mean absorbance/mg tissue) from homogenized cortical tissue derived from the hemisphere ipsilateral to CCI injury (n=6/group). Increased BBB permeability is observed in normal rats after cortical injury with preservation towards uninjured levels with MAPC therapy. The same experiment completed in animals after splenectomy failed to show the increase in BBB permeability with cortical injury. * indicates statistical significance compared to CCI injury alone control sample (ANOVA with Tukey Kramer post hoc, p<0.05).

It should be understood that this invention is not limited to the particular methodology, protocols, and reagents, etc., described herein and, as such, may vary. The terminology used herein is for the purpose of describing particular embodiments only, and is not intended to limit the scope of the disclosed invention, which is defined solely by the claims.

The section headings are used herein for organizational purposes only and are not to be construed as in any way limiting the subject matter described.

The methods and techniques of the present application are generally performed according to conventional methods well-known in the art and as described in various general and more specific references that are cited and discussed throughout the present specification unless otherwise indicated. See, e.g., Sambrook et al., *Molecular Cloning: A Laboratory Manual,* 3rd ed., Cold Spring Harbor Laboratory Press, Cold Spring Harbor, N.Y. (2001) and Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990).

Definitions

"A" or "an" means herein one or more than one; at least one. Where the plural form is used herein, it generally includes the singular.

A "cell bank" is industry nomenclature for cells that have been grown and stored for future use. Cells may be stored in aliquots. They can be used directly out of storage or may be expanded after storage. This is a convenience so that there are "off the shelf" cells available for administration. The cells may already be stored in a pharmaceutically-acceptable excipient so they may be directly administered or they may be mixed with an appropriate excipient when they are released from storage. Cells may be frozen or otherwise stored in a form to preserve viability. In one embodiment of the invention, cell banks are created in which the cells have been selected for enhanced potency to achieve the effects described in this application. Following release from storage, and prior to administration to the subject, it may be preferable to again assay the cells for potency. This can be done using any of the assays, direct or indirect, described in this application or otherwise known in the art. Then cells having the desired potency can then be administered to the subject for treatment. Banks can be made using cells derived from the individual to be treated (from their pre-natal tissues such as placenta, umbilical cord blood, or umbilical cord matrix or expanded from the individual at any time after birth). Or banks can contain cells for allogeneic uses.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of and similar phrases using words of the root "comprise" are used herein as synonyms of "comprising" and have the same meaning.

"Comprised of" is a synonym of "comprising" (see above).

"EC cells" were discovered from analysis of a type of cancer called a teratocarcinoma. In 1964, researchers noted that a single cell in teratocarcinomas could be isolated and remain undifferentiated in culture. This type of stem cell became known as an embryonic carcinoma cell (EC cell).

"Effective amount" generally means an amount which provides the desired local or systemic effect, e.g., effective to ameliorate undesirable effects of inflammation, including achieving the specific desired effects described in this application. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result.

"Embryonic Stem Cells (ESC)" are well known in the art and have been prepared from many different mammalian species. Embryonic stem cells are stem cells derived from the inner cell mass of an early stage embryo known as a blastocyst. They are able to differentiate into all derivatives of the three primary germ layers: ectoderm, endoderm, and mesoderm. These include each of the more than 220 cell types in the adult body. The ES cells can become any tissue in the body, excluding placenta. Only the morula's cells are totipotent, able to become all tissues and a placenta. Some cells similar to ESCs may be produced by nuclear transfer of a somatic cell nucleus into an enucleated fertilized egg.

Use of the term "includes" is not intended to be limiting.

"Increase" or "increasing" means to induce a biological event entirely or to increase the degree of the event.

"Induced pluripotent stem cells (IPSC or IPS cells)" are somatic cells that have been reprogrammed, for example, by introducing exogenous genes that confer on the somatic cell a less differentiated phenotype. These cells can then be induced to differentiate into less differentiated progeny. IPS cells have been derived using modifications of an approach originally discovered in 2006 (Yamanaka, S. et al., *Cell Stem Cell*, 1:39-49 (2007)). For example, in one instance, to create IPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., *PNAS*, 105:5856-5861 (2008); Jaenisch et al., *Cell*, 132:567-582 (2008); Hanna et al., *Cell*, 133:250-264 (2008); and Brambrink et al., *Cell Stem Cell*, 2:151-159 (2008). These references are incorporated by reference for teaching IPSCs and methods for producing them. It is also possible that such cells can be created by specific culture conditions (exposure to specific agents).

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only the cells of the invention. Rather, the term "isolated" indicates that the cells of the invention are removed from their natural tissue environment and are present at a higher concentration as compared to the normal tissue environment. Accordingly, an "isolated" cell population may further include cell types in addition to the cells of the invention cells and may include additional tissue components. This also can be expressed in terms of cell doublings, for example. A cell may have undergone 10, 20, 30, 40 or more doublings in vitro or ex vivo so that it is enriched compared to its original numbers in vivo or in its original tissue environment (e.g., bone marrow, peripheral blood, placenta, umbilical cord, umbilical cord blood, adipose tissue, etc.).

"MAPC" is an acronym for "multipotent adult progenitor cell." It refers to a cell that is not an embryonic stem cell or germ cell but has some characteristics of these. MAPC can be characterized in a number of alternative descriptions, each of which conferred novelty to the cells when they were discovered. They can, therefore, be characterized by one or more of those descriptions. First, they have extended replicative capacity in culture without being transformed (tumorigenic) and with a normal karyotype. Second, they may give rise to cell progeny of more than one germ layer, such as two or all three germ layers (i.e., endoderm, mesoderm and ectoderm) upon differentiation. Third, although they are not embryonic stem cells or germ cells, they may express markers of these primitive cell types so that MAPCs may express one or more of Oct 3/4 (i.e., Oct 3A), rex-1, and rox-1. They may also express one or more of sox-2 and SSEA-4. Fourth, like a stem cell, they may self-renew, that is, have an extended replication capacity without being transformed. This means that these cells express telomerase (i.e., have telomerase activity). Accordingly, the cell type that was designated "MAPC" may be characterized by alternative basic characteristics that describe the cell via some of its novel properties.

The term "adult" in MAPC is non-restrictive. It refers to a non-embryonic somatic cell. MAPCs are karyotypically normal and do not form teratomas in vivo. This acronym was first used in U.S. Pat. No. 7,015,037 to describe a pluripotent cell isolated from bone marrow. However, cells with pluripotential markers and/or differentiation potential have been discovered subsequently and, for purposes of this invention, may be equivalent to those cells first designated "MAPC." Essential descriptions of the MAPC type of cell are provided in the Summary of the Invention above.

MAPC represents a more primitive progenitor cell population than MSC (Verfaillie, C. M., *Trends Cell Biol* 12:502-8 (2002), Jahagirdar, B. N., et al., *Exp Hematol*, 29:543-56 (2001); Reyes, M. and C. M. Verfaillie, *Ann N Y Acad Sci*, 938:231-233 (2001); Jiang, Y. et al., *Exp Hematol*, 30896-904 (2002); and (Jiang, Y. et al., *Nature*, 418:41-9. (2002)).

The term "MultiStem®" is the trade name for a cell preparation based on the MAPCs of U.S. Pat. No. 7,015,037, i.e., a non-embryonic stem, non-germ cell as described above. MultiStem® is prepared according to cell culture methods disclosed in this patent application, particularly, lower oxygen and higher serum. MultiStem® is highly expandable, karyotypically normal, and does not form teratomas in vivo. It may differentiate into cell lineages of more than one germ layer and may express one or more of telomerase, oct3/4, rex-1, rox-1, sox-2, and SSEA4.

"Pharmaceutically-acceptable carrier" is any pharmaceutically-acceptable medium for the cells used in the present invention. Such a medium may retain isotonicity, cell metabolism, pH, and the like. It is compatible with administration to a subject in vivo, and can be used, therefore, for cell delivery and treatment.

The term "potency" refers to the ability of the cells to achieve the various effects described in this application. Accordingly, potency refers to the effect at various levels, including, but not limited to, reducing symptoms of inflammation, preserving splenic mass, increasing $CD4^+$ and $CD8^+$ T-cells in spleen, increasing anti-inflammatory cytokines, modulation of M1-M2 activation of macrophages, etc.

"Primordial embryonic germ cells" (PG or EG cells) can be cultured and stimulated to produce many less differentiated cell types.

"Progenitor cells" are cells produced during differentiation of a stem cell that have some, but not all, of the characteristics of their terminally-differentiated progeny. Defined progenitor cells, such as "cardiac progenitor cells," are committed to a lineage, but not to a specific or terminally differentiated cell type. The term "progenitor" as used in the acronym "MAPC" does not limit these cells to a particular lineage. A progenitor cell can form a progeny cell that is more highly differentiated than the progenitor cell.

The term "reduce" as used herein means to prevent as well as decrease. In the context of treatment, to "reduce" is to either prevent or ameliorate one or more clinical symptoms. A clinical symptom is one (or more) that has or will have, if left untreated, a negative impact on the quality of life (health) of the subject. This also applies to the underlying biological effects such as reducing pro-inflammatory molecules, activation of macrophages, etc., the end result of which would be to ameliorate the deleterious effects of inflammation.

"Selecting" a cell with a desired level of potency (e.g., for modulating activation of macrophages) can mean identifying (as by assay), isolating, and expanding a cell. This could create a population that has a higher potency than the parent cell population from which the cell was isolated. The "parent" cell population refers to the parent cells from which the selected cells divided. "Parent" refers to an actual P1→F1 relationship (i.e., a progeny cell). So if cell X is isolated from a mixed population of cells X and Y, in which X is an expressor and Y is not, one would not classify a mere isolate of X as having enhanced expression. But, if a progeny cell of X is a higher expressor, one would classify the progeny cell as having enhanced expression.

To select a cell that achieves the desired effect would include both an assay to determine if the cells achieve the desired effect and would also include obtaining those cells. The cell may naturally achieve the desired effect in that the effect is not achieved by an exogenous transgene/DNA. But an effective cell may be improved by being incubated with or exposed to an agent that increases the effect. The cell population from which the effective cell is selected may not be known to have the potency prior to conducting the assay. The cell may not be known to achieve the desired effect prior to conducting the assay. As an effect could depend on gene expression and/or secretion, one could also select on the basis of one or more of the genes that cause the effect.

Selection could be from cells in a tissue. For example, in this case, cells would be isolated from a desired tissue, expanded in culture, selected for achieving the desired effect, and the selected cells further expanded.

Selection could also be from cells ex vivo, such as cells in culture. In this case, one or more of the cells in culture would be assayed for achieving the desired effect and the cells obtained that achieve the desired effect could be further expanded.

Cells could also be selected for enhanced ability to achieve the desired effect. In this case, the cell population from which the enhanced cell is obtained already has the desired effect. Enhanced effect means a higher average amount per cell than in the parent population.

The parent population from which the enhanced cell is selected may be substantially homogeneous (the same cell type). One way to obtain such an enhanced cell from this population is to create single cells or cell pools and assay those cells or cell pools to obtain clones that naturally have the enhanced (greater) effect (as opposed to treating the cells with a modulator that induces or increases the effect) and then expanding those cells that are naturally enhanced.

However, cells may be treated with one or more agents that will induce or increase the effect. Thus, substantially homogeneous populations may be treated to enhance the effect.

If the population is not substantially homogeneous, then, it is preferable that the parental cell population to be treated contains at least 100 of the desired cell type in which enhanced effect is sought, more preferably at least 1,000 of the cells, and still more preferably, at least 10,000 of the cells. Following treatment, this sub-population can be recovered from the heterogeneous population by known cell selection techniques and further expanded if desired.

Thus, desired levels of effect may be those that are higher than the levels in a given preceding population. For example, cells that are put into primary culture from a tissue and expanded and isolated by culture conditions that are not specifically designed to produce the effect may provide a parent population. Such a parent population can be treated to enhance the average effect per cell or screened for a cell or cells within the population that express greater degrees of effect without deliberate treatment. Such cells can be expanded then to provide a population with a higher (desired) expression.

"Self-renewal" of a stem cell refers to the ability to produce replicate daughter stem cells having differentiation potential that is identical to those from which they arose. A similar term used in this context is "proliferation."

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has de-differentiated, for example, by nuclear transfer, by fusion with a more primitive stem cell, by introduction of specific transcription factors, or by culture under specific conditions. See, for example, Wilmut et al., *Nature,* 385: 810-813 (1997); Ying et al., *Nature,* 416:545-548 (2002); Guan et al., *Nature,* 440:1199-1203 (2006); Takahashi et al., *Cell,* 126:663-676 (2006); Okita et al., *Nature,* 448:313-317 (2007); and Takahashi et al., *Cell,* 131:861-872 (2007).

Dedifferentiation may also be caused by the administration of certain compounds or exposure to a physical environment in vitro or in vivo that would cause the dedifferentiation. Stem cells also may be derived from abnormal tissue, such as a teratocarcinoma and some other sources such as embryoid bodies (although these can be considered embryonic stem cells in that they are derived from embryonic tissue, although not directly from the inner cell mass). Stem cells may also be produced by introducing genes associated with stem cell function into a non-stem cell, such as an induced pluripotent stem cell.

"Subject" means a vertebrate, such as a mammal, such as a human. Mammals include, but are not limited to, humans, dogs, cats, horses, cows, and pigs.

The term "therapeutically effective amount" refers to the amount of an agent determined to produce any therapeutic response in a mammal. For example, effective anti-inflammatory therapeutic agents may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are readily ascertained by one of ordinary skill in the art. Thus, to "treat" means to deliver such an amount. Thus, treating can prevent or ameliorate any pathological symptoms of inflammation.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

"Validate" means to confirm. In the context of the invention, one confirms that a cell is an expressor with a desired potency. This is so that one can then use that cell (in treatment, banking, drug screening, etc.) with a reasonable expectation of efficacy. Accordingly, to validate means to confirm that the cells, having been originally found to have/established as having the desired activity, in fact, retain that activity. Thus, validation is a verification event in a two-event process involving the original determination and the follow-up determination. The second event is referred to herein as "validation."

Stem Cells

The present invention can be practiced, preferably, using stem cells of vertebrate species, such as humans, non-human primates, domestic animals, livestock, and other non-human mammals. These include, but are not limited to, those cells described below.

Embryonic Stem Cells

The most well studied stem cell is the embryonic stem cell (ESC) as it has unlimited self-renewal and multipotent differentiation potential. These cells are derived from the inner cell mass of the blastocyst or can be derived from the primordial germ cells of a post-implantation embryo (embryonal germ cells or EG cells). ES and EG cells have been derived, first from mouse, and later, from many different animals, and more recently, also from non-human primates and humans. When introduced into mouse blastocysts or blastocysts of other animals, ESCs can contribute to all tissues of the animal. ES and EG cells can be identified by positive staining with antibodies against SSEA1 (mouse) and SSEA4 (human). See, for example, U.S. Pat. Nos. 5,453,357; 5,656,479; 5,670,372; 5,843,780; 5,874,301; 5,914,268; 6,110,739 6,190,910; 6,200,806; 6,432,711; 6,436,701; 6,500,668; 6,703,279; 6,875,607; 7,029,913; 7,112,437; 7,145,057; 7,153,684; and 7,294,508, each of which is incorporated by reference for teaching embryonic stem cells and methods of making and expanding them. Accordingly, ESCs and methods for isolating and expanding them are well-known in the art.

A number of transcription factors and exogenous cytokines have been identified that influence the potency status of embryonic stem cells in vivo. The first transcription factor to be described that is involved in stem cell pluripotency is Oct4. Oct4 belongs to the POU (Pit-Oct-Unc) family of transcription factors and is a DNA binding protein that is able to activate the transcription of genes, containing an octameric sequence called "the octamer motif" within the promoter or enhancer region. Oct4 is expressed at the moment of the cleavage stage of the fertilized zygote until the egg cylinder is formed. The function of Oct3/4 is to repress differentiation inducing genes (i.e., FoxaD3, hCG) and to activate genes promoting pluripotency (FGF4, Utf1, Rex1). Sox2, a member of the high mobility group (HMG) box transcription factors, cooperates with Oct4 to activate transcription of genes expressed in the inner cell mass. It is essential that Oct3/4 expression in embryonic stem cells is maintained between certain levels. Overexpression or downregulation of >50% of Oct4 expression level will alter embryonic stem cell fate, with the formation of primitive endoderm/mesoderm or trophectoderm, respectively. In vivo, Oct4 deficient embryos develop to the blastocyst stage, but the inner cell mass cells are not pluripotent. Instead they differentiate along the extraembryonic trophoblast lineage. Sall4, a mammalian Spalt transcription factor, is an upstream regulator of Oct4, and is therefore important to maintain appropriate levels of Oct4 during early phases of embryology. When Sall4 levels fall below a certain threshold, trophectodermal cells will expand ectopically into the inner cell mass. Another transcription factor required for pluripotency is Nanog, named after a celtic tribe "Tir Nan Og": the land of the ever young. In vivo, Nanog is expressed from the stage of the compacted morula, is subsequently defined to the inner cell mass and is downregulated by the implantation stage. Downregulation of Nanog may be important to avoid an uncontrolled expansion of pluripotent cells and to allow multilineage differentiation during gastrulation. Nanog null embryos, isolated at day 5.5, consist of a disorganized blastocyst, mainly containing extraembryonic endoderm and no discernable epiblast.

Non-Embryonic Stem Cells

Stem cells have been identified in most tissues. Perhaps the best characterized is the hematopoietic stem cell (HSC). HSCs are mesoderm-derived cells that can be purified using cell surface markers and functional characteristics. They have been isolated from bone marrow, peripheral blood, cord blood, fetal liver, and yolk sac. They initiate hematopoiesis and generate multiple hematopoietic lineages. When transplanted into lethally-irradiated animals, they can repopulate the erythroid neutrophil-macrophage, megakaryocyte, and lymphoid hematopoietic cell pool. They can also be induced to undergo some self-renewal cell division. See, for example, U.S. Pat. Nos. 5,635,387; 5,460, 964; 5,677,136; 5,750,397; 5,681,599; and 5,716,827. U.S. Pat. No. 5,192,553 reports methods for isolating human neonatal or fetal hematopoietic stem or progenitor cells. U.S. Pat. No. 5,716,827 reports human hematopoietic cells that are Thy-1$^+$ progenitors, and appropriate growth media to regenerate them in vitro. U.S. Pat. No. 5,635,387 reports a method and device for culturing human hematopoietic cells and their precursors. U.S. Pat. No. 6,015,554 describes a method of reconstituting human lymphoid and dendritic cells. Accordingly, HSCs and methods for isolating and expanding them are well-known in the art.

Another stem cell that is well-known in the art is the neural stem cell (NSC). These cells can proliferate in vivo and continuously regenerate at least some neuronal cells. When cultured ex vivo, neural stem cells can be induced to proliferate as well as differentiate into different types of neurons and glial cells. When transplanted into the brain, neural stem cells can engraft and generate neural and glial cells. See, for example, Gage F. H., *Science*, 287:1433-1438 (2000), Svendsen S. N. et al, *Brain Pathology*, 9:499-513 (1999), and Okabe S. et al., *Mech Development*, 59:89-102 (1996). U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,564,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain. Accordingly, neural stem cells and methods for making and expanding them are well-known in the art.

Another stem cell that has been studied extensively in the art is the mesenchymal stem cell (MSC). MSCs are derived from the embryonal mesoderm and can be isolated from many sources, including adult bone marrow, peripheral blood, fat, placenta, and umbilical blood, among others. MSCs can differentiate into many mesodermal tissues, including muscle, bone, cartilage, fat, and tendon. There is considerable literature on these cells. See, for example, U.S. Pat. Nos. 5,486,389; 5,827,735; 5,811,094; 5,736,396; 5,837,539; 5,837,670; and 5,827,740. See also Pittenger, M. et al, *Science*, 284:143-147 (1999).

Another example of an adult stem cell is adipose-derived adult stem cells (ADSCs) which have been isolated from fat, typically by liposuction followed by release of the ADSCs using collagenase. ADSCs are similar in many ways to MSCs derived from bone marrow, except that it is possible to isolate many more cells from fat. These cells have been reported to differentiate into bone, fat, muscle, cartilage, and neurons. A method of isolation has been described in U.S. 2005/0153442.

Other stem cells that are known in the art include gastrointestinal stem cells, epidermal stem cells, and hepatic stem cells, which have also been termed "oval cells" (Potten, C., et al., *Trans R Soc Lond B Biol Sci*, 353:821-830 (1998), Watt, F., *Trans R Soc Lond B Biol Sci*, 353:831 (1997); Alison et al., *Hepatology*, 29:678-683 (1998).

Other non-embryonic cells reported to be capable of differentiating into cell types of more than one embryonic germ layer include, but are not limited to, cells from umbilical cord blood (see U.S. Publication No. 2002/0164794), placenta (see U.S. Publication No. 2003/0181269, umbilical cord matrix (Mitchell, K. E. et al., *Stem Cells*, 21:50-60 (2003)), small embryonic-like stem cells (Kucia, M. et al., *J Physiol Pharmacol*, 57 Suppl 5:5-18 (2006)), amniotic fluid stem cells (Atala, A., *J Tissue Regen Med*, 1:83-96 (2007)), skin-derived precursors (Toma et al., *Nat Cell Biol*, 3:778-784 (2001)), and bone marrow (see U.S. Publication Nos. 2003/0059414 and 2006/0147246), each of which is incorporated by reference for teaching these cells.

Strategies of Reprogramming Somatic Cells

Several different strategies such as nuclear transplantation, cellular fusion, and culture induced reprogramming have been employed to induce the conversion of differentiated cells into an embryonic state. Nuclear transfer involves the injection of a somatic nucleus into an enucleated oocyte, which, upon transfer into a surrogate mother, can give rise to a clone ("reproductive cloning"), or, upon explantation in culture, can give rise to genetically matched embryonic stem (ES) cells ("somatic cell nuclear transfer," SCNT). Cell fusion of somatic cells with ES cells results in the generation of hybrids that show all features of pluripotent ES cells. Explantation of somatic cells in culture selects for immortal cell lines that may be pluripotent or multipotent. At present, spermatogonial stem cells are the only source of pluripotent cells that can be derived from postnatal animals. Transduction of somatic cells with defined factors can initiate reprogramming to a pluripotent state. These experimental approaches have been extensively reviewed (Hochedlinger and Jaenisch, *Nature*, 441:1061-1067 (2006) and Yamanaka, S., *Cell Stem Cell*, 1:39-49 (2007)).

Nuclear Transfer

Nuclear transplantation (NT), also referred to as somatic cell nuclear transfer (SCNT), denotes the introduction of a nucleus from a donor somatic cell into an enucleated ogocyte to generate a cloned animal such as Dolly the sheep (Wilmut et al., *Nature*, 385:810-813 (1997). The generation of live animals by NT demonstrated that the epigenetic state of somatic cells, including that of terminally differentiated cells, while stable, is not irreversible fixed but can be reprogrammed to an embryonic state that is capable of directing development of a new organism. In addition to providing an exciting experimental approach for elucidating the basic epigenetic mechanisms involved in embryonic development and disease, nuclear cloning technology is of potential interest for patient-specific transplantation medicine.

Fusion of Somatic Cells and Embryonic Stem Cells

Epigenetic reprogramming of somatic nuclei to an undifferentiated state has been demonstrated in murine hybrids produced by fusion of embryonic cells with somatic cells. Hybrids between various somatic cells and embryonic carcinoma cells (Solter, D., *Nat Rev Genet*, 7:319-327 (2006), embryonic germ (EG), or ES cells (Zwaka and Thomson, *Development*, 132:227-233 (2005)) share many features with the parental embryonic cells, indicating that the pluripotent phenotype is dominant in such fusion products. As with mouse (Tada et al., *Curr Biol*, 11:1553-1558 (2001)), human ES cells have the potential to reprogram somatic nuclei after fusion (Cowan et al., *Science*, 309:1369-1373 (2005)); Yu et al., *Science*, 318:1917-1920 (2006)). Activation of silent pluripotency markers such as Oct4 or reactivation of the inactive somatic X chromosome provided molecular evidence for reprogramming of the somatic genome in the hybrid cells. It has been suggested that DNA replication is essential for the activation of pluripotency markers, which is first observed 2 days after fusion (Do and Scholer, *Stem Cells*, 22:941-949 (2004)), and that forced overexpression of Nanog in ES cells promotes pluripotency when fused with neural stem cells (Silva et al., *Nature*, 441:997-1001 (2006)).

Culture-Induced Reprogramming

Pluripotent cells have been derived from embryonic sources such as blastomeres and the inner cell mass (ICM) of the blastocyst (ES cells), the epiblast (EpiSC cells), primordial germ cells (EG cells), and postnatal spermatogonial stem cells ("maGSCsm" "ES-like" cells). The following pluripotent cells, along with their donor cell/tissue is as follows: parthogenetic ES cells are derived from murine oocytes (Narasimha et al., *Curr Biol*, 7:881-884 (1997));

embryonic stem cells have been derived from blastomeres (Wakayama et al., *Stem Cells*, 25:986-993 (2007)); inner cell mass cells (source not applicable) (Eggan et al., *Nature*, 428:44-49 (2004)); embryonic germ and embryonal carcinoma cells have been derived from primordial germ cells (Matsui et al., *Cell*, 70:841-847 (1992)); GMCS, maSSC, and MASC have been derived from spermatogonial stem cells (Guan et al., *Nature*, 440:1199-1203 (2006); Kanatsu-Shinohara et al., *Cell*, 119:1001-1012 (2004); and Seandel et al., *Nature*, 449:346-350 (2007)); EpiSC cells are derived from epiblasts (Brons et al., *Nature*, 448:191-195 (2007); Tesar et al., *Nature*, 448:196-199 (2007)); parthogenetic ES cells have been derived from human oocytes (Cibelli et al., *Science*, 295L819 (2002); Revazova et al., *Cloning Stem Cells*, 9:432-449 (2007)); human ES cells have been derived from human blastocysts (Thomson et al., *Science*, 282:1145-1147 (1998)); MAPC have been derived from bone marrow (Jiang et al., *Nature*, 418:41-49 (2002); Phinney and Prockop, *Stem Cells*, 25:2896-2902 (2007)); cord blood cells (derived from cord blood) (van de Ven et al., *Exp Hematol*, 35:1753-1765 (2007)); neurosphere derived cells derived from neural cell (Clarke et al., *Science*, 288:1660-1663 (2000)). Donor cells from the germ cell lineage such as PGCs or spermatogonial stem cells are known to be unipotent in vivo, but it has been shown that pluripotent ES-like cells (Kanatsu-Shinohara et al., *Cell*, 119:1001-1012 (2004) or maGSCs (Guan et al., *Nature*, 440:1199-1203 (2006), can be isolated after prolonged in vitro culture. While most of these pluripotent cell types were capable of in vitro differentiation and teratoma formation, only ES, EG, EC, and the spermatogonial stem cell-derived maGCSs or ES-like cells were pluripotent by more stringent criteria, as they were able to form postnatal chimeras and contribute to the germline. Recently, multipotent adult spermatogonial stem cells (MASCs) were derived from testicular spermatogonial stem cells of adult mice, and these cells had an expression profile different from that of ES cells (Seandel et al., *Nature*, 449:346-350 (2007)) but similar to EpiSC cells, which were derived from the epiblast of postimplantation mouse embryos (Brons et al., *Nature*, 448:191-195 (2007); Tesar et al., *Nature*, 448:196-199 (2007)).

Reprogramming by Defined Transcription Factors

Takahashi and Yamanaka have reported reprogramming somatic cells back to an ES-like state (Takahashi and Yamanaka, *Cell*, 126:663-676 (2006)). They successfully reprogrammed mouse embryonic fibroblasts (MEFs) and adult fibroblasts to pluripotent ES-like cells after viral-mediated transduction of the four transcription factors Oct4, Sox2, c-myc, and Klf4 followed by selection for activation of the Oct4 target gene Fbx15 (FIG. 2A). Cells that had activated Fbx15 were coined iPS (induced pluripotent stem) cells and were shown to be pluripotent by their ability to form teratomas, although they were unable to generate live chimeras. This pluripotent state was dependent on the continuous viral expression of the transduced Oct4 and Sox2 genes, whereas the endogenous Oct4 and Nanog genes were either not expressed or were expressed at a lower level than in ES cells, and their respective promoters were found to be largely methylated. This is consistent with the conclusion that the Fbx15-iPS cells did not correspond to ES cells but may have represented an incomplete state of reprogramming. While genetic experiments had established that Oct4 and Sox2 are essential for pluripotency (Chambers and Smith, *Oncogene*, 23:7150-7160 (2004); Ivanona et al., *Nature*, 442:5330538 (2006); Masui et al., *Nat Cell Biol*, 9:625-635 (2007)), the role of the two oncogenes c-myc and Klf4 in reprogramming is less clear. Some of these oncogenes may, in fact, be dispensable for reprogramming, as both mouse and human iPS cells have been obtained in the absence of c-myc transduction, although with low efficacy (Nakagawa et al., *Nat Biotechnol*, 26:191-106 (2008); Werning et al., *Nature*, 448:318-324 (2008); Yu et al., *Science*, 318: 1917-1920 (2007)).

MAPC

Human MAPCs are described in U.S. Pat. No. 7,015,037. MAPCs have been identified in other mammals. Murine MAPCs, for example, are also described in U.S. Pat. No. 7,015,037. Rat MAPCs are also described in U.S. Pat. No. 7,838,289.

These references are incorporated by reference for describing MAPCs first isolated by Catherine Verfaillie.

Isolation and Growth of MAPCs

Methods of MAPC isolation are known in the art. See, for example, U.S. Pat. No. 7,015,037, and these methods, along with the characterization (phenotype) of MAPCs, are incorporated herein by reference. MAPCs can be isolated from multiple sources, including, but not limited to, bone marrow, placenta, umbilical cord and cord blood, muscle, brain, liver, spinal cord, blood or skin. It is, therefore, possible to obtain bone marrow aspirates, brain or liver biopsies, and other organs, and isolate the cells using positive or negative selection techniques available to those of skill in the art, relying upon the genes that are expressed (or not expressed) in these cells (e.g., by functional or morphological assays such as those disclosed in the above-referenced applications, which have been incorporated herein by reference).

MAPCs have also been obtained my modified methods described in Breyer et al., *Experimental Hematology*, 34:1596-1601 (2006) and Subramanian et al., Cellular Programming and Reprogramming: Methods and Protocols; S. Ding (ed.), *Methods in Molecular Biology*, 636:55-78 (2010), incorporated by reference for these methods.

MAPCs from Human Bone Marrow as Described in U.S. Pat. No. 7,015,037

MAPCs do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of $CD45^+$ and $Gly-A^+$ cells, and the remaining approximately 0.1% of marrow mononuclear cells were then recovered. Cells could also be plated in fibronectin-coated wells and cultured as described below for 2-4 weeks to deplete the cells of $CD45^+$ and $Gly-A^+$ cells. In cultures of adherent bone marrow cells, many adherent stromal cells undergo replicative senescence around cell doubling 30 and a more homogenous population of cells continues to expand and maintains long telomeres.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch et al., 1983 (immunoaffinity chromatography), and Wysocki and Sato, 1978 (fluorescence-activated cell sorting).

Cells may be cultured in low-serum or serum-free culture medium. Serum-free medium used to culture MAPCs is described in U.S. Pat. No. 7,015,037. Commonly-used growth factors include but are not limited to platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference for teaching growing cells in serum-free medium.

Additional Culture Methods

In additional experiments the density at which MAPCs are cultured can vary from about 100 cells/cm$^2$ or about 150 cells/cm$^2$ to about 10,000 cells/cm$^2$, including about 200 cells/cm$^2$ to about 1500 cells/cm$^2$ to about 2000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 1-5% and, especially, 3-5%, can be used at any time during the isolation, growth and differentiation of MAPCs in culture.

Cells may be cultured under various serum concentrations, e.g., about 2-20%. Fetal bovine serum may be used. Higher serum may be used in combination with lower oxygen tensions, for example, about 15-20%. Cells need not be selected prior to adherence to culture dishes. For example, after a Ficoll gradient, cells can be directly plated, e.g., 250,000-500,000/cm$^2$. Adherent colonies can be picked, possibly pooled, and expanded.

In one embodiment, used in the experimental procedures in the Examples, high serum (around 15-20%) and low oxygen (around 3-5%) conditions were used for the cell culture. Specifically, adherent cells from colonies were plated and passaged at densities of about 1700-2300 cells/cm$^2$ in 18% serum and 3% oxygen (with PDGF and EGF).

In an embodiment specific for MAPCs, supplements are cellular factors or components that allow MAPCs to retain the ability to differentiate into cell types of more than one embryonic lineage, such as all three lineages. This may be indicated by the expression of specific markers of the undifferentiated state, such as Oct 3/4 (Oct 3A) and/or markers of high expansion capacity, such as telomerase.

Cell Culture

For all the components listed below, see U.S. Pat. No. 7,015,037, which is incorporated by reference for teaching these components.

In general, cells useful for the invention can be maintained and expanded in culture medium that is available and well-known in the art. Also contemplated is supplementation of cell culture medium with mammalian sera. Additional supplements can also be used advantageously to supply the cells with the necessary trace elements for optimal growth and expansion. Hormones can also be advantageously used in cell culture. Lipids and lipid carriers can also be used to supplement cell culture media, depending on the type of cell and the fate of the differentiated cell. Also contemplated is the use of feeder cell layers.

Cells in culture can be maintained either in suspension or attached to a solid support, such as extracellular matrix components. Stem cells often require additional factors that encourage their attachment to a solid support, such as type I and type II collagen, chondroitin sulfate, fibronectin, "superfibronectin" and fibronectin-like polymers, gelatin, poly-D and poly-L-lysine, thrombospondin and vitronectin. One embodiment of the present invention utilizes fibronectin. See, for example, Ohashi et al., *Nature Medicine*, 13:880-885 (2007); Matsumoto et al., *J Bioscience and Bioengineering*, 105:350-354 (2008); Kirouac et al., *Cell Stem Cell*, 3:369-381 (2008); Chua et al., *Biomaterials*, 26:2537-2547 (2005); Drobinskaya et al., *Stem Cells*, 26:2245-2256 (2008); Dvir-Ginzberg et al., FASEB J, 22:1440-1449 (2008); Turner et al., *J Biomed Mater Res Part B: Appl Biomater*, 82B:156-168 (2007); and Miyazawa et al., *Journal of Gastroenterology and Hepatology*, 22:1959-1964 (2007)).

Cells may also be grown in "3D" (aggregated) cultures. An example is PCT/US2009/31528, filed Jan. 21, 2009.

Once established in culture, cells can be used fresh or frozen and stored as frozen stocks, using, for example, DMEM with 40% FCS and 10% DMSO. Other methods for preparing frozen stocks for cultured cells are also available to those of skill in the art.

Pharmaceutical Formulations

U.S. Pat. No. 7,015,037 is incorporated by reference for teaching pharmaceutical formulations. In certain embodiments, the cell populations are present within a composition adapted for and suitable for delivery, i.e., physiologically compatible.

In some embodiments the purity of the cells (or conditioned medium) for administration to a subject is about 100% (substantially homogeneous). In other embodiments it is 95% to 100%. In some embodiments it is 85% to 95%. Particularly, in the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The choice of formulation for administering the cells for a given application will depend on a variety of factors. Prominent among these will be the species of subject, the nature of the condition being treated, its state and distribution in the subject, the nature of other therapies and agents that are being administered, the optimum route for administration, survivability via the route, the dosing regimen, and other factors that will be apparent to those skilled in the art. For instance, the choice of suitable carriers and other additives will depend on the exact route of administration and the nature of the particular dosage form.

Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant.

In some embodiments, cells/medium are formulated in a unit dosage injectable form, such as a solution, suspension, or emulsion. Pharmaceutical formulations suitable for injection of cells/medium typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

In some embodiments cells are encapsulated for administration, particularly where encapsulation enhances the effectiveness of the therapy, or provides advantages in handling and/or shelf life. Cells may be encapsulated by membranes, as well as capsules, prior to implantation. It is contemplated that any of the many methods of cell encapsulation available may be employed.

A wide variety of materials may be used in various embodiments for microencapsulation of cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of cells are known to those of skill in the art and are described, for example, in Chang, P., et al., 1999; Matthew, H. W., et al., 1991; Yanagi, K., et al., 1989; Cai Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of cells.

Certain embodiments incorporate cells into a polymer, such as a biopolymer or synthetic polymer. Examples of biopolymers include, but are not limited to, fibronectin, fibrin, fibrinogen, thrombin, collagen, and proteoglycans. Other factors, such as the cytokines discussed above, can also be incorporated into the polymer. In other embodiments of the invention, cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

The dosage of the cells will vary within wide limits and will be fitted to the individual requirements in each particular case. In general, in the case of parenteral administration, it is customary to administer from about 0.01 to about 20 million cells/kg of recipient body weight. The number of cells will vary depending on the weight and condition of the recipient, the number or frequency of administrations, and other variables known to those of skill in the art. The cells can be administered by a route that is suitable for the tissue or organ. For example, they can be administered systemically, i.e., parenterally, by intravenous administration, or can be targeted to a particular tissue or organ; they can be administrated via subcutaneous administration or by administration into specific desired tissues.

The cells can be suspended in an appropriate excipient in a concentration from about 0.01 to about $5\times10^6$ cells/ml. Suitable excipients for injection solutions are those that are biologically and physiologically compatible with the cells and with the recipient, such as buffered saline solution or other suitable excipients. The composition for administration can be formulated, produced, and stored according to standard methods complying with proper sterility and stability.

Administration into Lymphohematopoietic Tissues

Techniques for administration into these tissues are known in the art. For example, intra-bone marrow injections can involve injecting cells directly into the bone marrow cavity typically of the posterior iliac crest but may include other sites in the iliac crest, femur, tibia, humerus, or ulna; splenic injections could involve radiographic guided injections into the spleen or surgical exposure of the spleen via laparoscopic or laparotomy; Peyer's patches, GALT, or BALT injections could require laparotomy or laparoscopic injection procedures.

Dosing

Doses for humans or other mammals can be determined without undue experimentation by the skilled artisan, from this disclosure, the documents cited herein, and the knowledge in the art. The dose of cells/medium appropriate to be used in accordance with various embodiments of the invention will depend on numerous factors. The parameters that will determine optimal doses to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the cells are syngeneic, autologous, allogeneic, or xenogeneic; their potency (specific activity); the site and/or distribution that must be targeted for the cells/medium to be effective; and such characteristics of the site such as accessibility to cells/medium and/or engraftment of cells. Additional parameters include co-administration with other factors (such as growth factors and cytokines). The optimal dose in a given situation also will take into consideration the way in which the cells/medium are formulated, the way they are administered, and the degree to which the cells/medium will be localized at the target sites following administration.

The optimal dose of cells could be in the range of doses used for autologous, mononuclear bone marrow transplantation. For fairly pure preparations of cells, optimal doses in various embodiments will range from $10^4$ to $10^8$ cells/kg of recipient mass per administration. In some embodiments the optimal dose per administration will be between $10^5$ to $10^7$ cells/kg. In many embodiments the optimal dose per administration will be $5\times10^5$ to $5\times10^6$ cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

In various embodiments, cells/medium may be administered in an initial dose, and thereafter maintained by further administration. Cells/medium may be administered by one method initially, and thereafter administered by the same method or one or more different methods. The levels can be maintained by the ongoing administration of the cells/medium. Various embodiments administer the cells/medium either initially or to maintain their level in the subject or both by intravenous injection. In a variety of embodiments, other forms of administration are used, dependent upon the patient's condition and other factors, discussed elsewhere herein.

Cells/medium may be administered in many frequencies over a wide range of times. Generally lengths of treatment will be proportional to the length of the disease process, the effectiveness of the therapies being applied, and the condition and response of the subject being treated.

Uses

Administering the cells is useful to reduce undesirable inflammation in any number of pathologies, including, but not limited to, colitis, alveolitis, bronchiolitis obliterans, ileitis, pancreatitis, glomerulonephritis, uveitis, arthritis, hepatitis, dermatitis, and enteritis, acute and chronic conditions in cardiovascular, e.g., acute myocardial infarction; peripheral vascular disease; pulmonary, e.g., asthma, ARDS; autoimmune, e.g., rheumatoid arthritis, multiple sclerosis, lupus, sclerodoma; psoriasis; gastrointestinal, e.g., graft-versus-host-disease, Crohn's disease, diabetes, ulcerative colitis, acute and chronic transplantation rejection, dermatitis, colitis, alveolitis, bronchiolitis obliterans, ileitis, pancreatitis, glomerulonephritis, uveitis, arthritis, hepatitis, dermatitis, and enteritis.

Administering the cells is useful to reduce undesirable inflammation in any number of CNS pathologies, including, but not limited to, ischemic stroke, multiple sclerosis, Alzheimer's Disease, ALS, Parkinson's Disease, hypoxic-ischemia, neonatal hypoxic ischemia, and traumatic brain or spinal cord injury.

In addition, other uses are provided by knowledge of the biological mechanisms described in this application. One of these includes drug discovery. This aspect involves screening one or more compounds for the ability to affect the cell's ability to achieve any of the effects described in this application. Accordingly, the assay may be designed to be conducted in vivo or in vitro. Assays could assess the effect at any desired level, e.g., morphological, e.g., in macrophage, $CD4^+$, and $CD8^+$ T-cells appearance and numbers, gene expression in a target, e.g., macrophages, functional, e.g., macrophage activation, IL-10, IL-4 in circulation, etc.

In a specific embodiment, the cells are screened for an agent that enhances the cells' ability to up-regulate IL-10 and/or down-regulate IL-6 and/or IL-1β. Regulating the expression of these molecules can be in the context of regulating the expression of these molecules in vivo, such as in a disease context, for example, stroke. Or regulating the expression of these molecules can be in an in vitro context, such as regulating expression of these molecules produced in other cell types that are exposed to the cells of the invention, or medium conditioned by the cells of the invention, or extracts of such conditioned medium.

Gene expression can be assessed by directly assaying protein or RNA. This can be done through any of the well-known techniques available in the art, such as by FACS and other antibody-based detection methods and PCR and other hybridization-based detection methods. Indirect assays may also be used for expression, such as the effect of gene expression.

Assays for potency may be performed by detecting the genes modulated by the cells. These may include, but are not limited to, oxygen radicals, NO, TNFα, Glu, quinolic acid, histamine, eicosanoids, NGF, BDNF, NT-4/5, TGFβ, GDNF, CNTF, IL-6, LIF, bFGF, HGF, PGn, IL-3, MMP-9, iNOS, CD16, CD86, CD64, and CD32, scavenger receptor A, CD163, arginase 1, CD14, CD206, CD23, and scavenger receptor B. Detection may be direct, e.g., via RNA or protein assays or indirect, e.g., biological assays for one or more biological effects of these genes.

Assays for expression/secretion of modulatory factors include, but are not limited to, ELISA, Luminex qRT-PCR, anti-factor western blots, and factor immunohistochemistry on tissue samples or cells.

Quantitative determination of modulatory factors in cells and conditioned media can be performed using commercially available assay kits (e.g., R&D Systems that relies on a two-step subtractive antibody-based assay).

A further use for the invention is the establishment of cell banks to provide cells for clinical administration. Generally, a fundamental part of this procedure is to provide cells that have a desired potency for administration in various therapeutic clinical settings.

In a specific embodiment of the invention, the cells are selected for having a desired potency for down-regulating IL-6 and/or IL-1β and/or upregulating IL-10. Up- and down-regulation can be in the context of regulating the expression of these molecules in vivo, such as in a disease context, for example, stroke. Or regulating the expression of these molecules can be in an in vitro context, such as regulating expression of these molecules produced in other cell types that are exposed to the cells of the invention, or medium conditioned by the cells of the invention, or extracts of such conditioned medium.

Any of the same assays useful for drug discovery could also be applied to selecting cells for the bank as well as from the bank for administration.

Accordingly, in a banking procedure, the cells (or medium) would be assayed for the ability to achieve any of the above effects. Then, cells would be selected that have a desired potency for any of the above effects, and these cells would form the basis for creating a cell bank.

It is also contemplated that potency can be increased by treatment with an exogenous compound, such as a compound discovered through screening the cells with large combinatorial libraries. These compound libraries may be libraries of agents that include, but are not limited to, small organic molecules, antisense nucleic acids, siRNA DNA aptamers, peptides, antibodies, non-antibody proteins, cytokines, chemokines, and chemo-attractants. For example, cells may be exposed such agents at any time during the growth and manufacturing procedure. The only requirement is that there be sufficient numbers for the desired assay to be conducted to assess whether or not the agent increases potency. Such an agent, found during the general drug discovery process described above, could more advantageously be applied during the last passage prior to banking.

One embodiment that has been applied successfully to MultiStem® is as follows. Cells can be isolated from a qualified marrow donor that has undergone specific testing requirements to determine that a cell product that is obtained from this donor would be safe to be used in a clinical setting. The mononuclear cells are isolated using either a manual or automated procedure. These mononuclear cells are placed in culture allowing the cells to adhere to the treated surface of a cell culture vessel. The MultiStem® cells are allowed to expand on the treated surface with media changes occurring on day 2 and day 4. On day 6, the cells are removed from the treated substrate by either mechanical or enzymatic means and replated onto another treated surface of a cell culture vessel. On days 8 and 10, the cells are removed from the treated surface as before and replated. On day 13, the cells are removed from the treated surface, washed and combined with a cryoprotectant material and frozen, ultimately, in liquid nitrogen. After the cells have been frozen for at least one week, an aliquot of the cells is removed and tested for potency, identity, sterility and other tests to determine the usefulness of the cell bank. These cells in this bank can then be used by thawing them, placing them in culture or use them out of the freeze to treat potential indications.

Another use is a diagnostic assay for efficacy and beneficial clinical effect following administration of the cells. Depending on the indication, there may be biomarkers available to assess. The dosage of the cells can be adjusted during the treatment according to the effect.

In a specific embodiment, the diagnostic assay involves assessing up-regulation of IL-10 and/or IL-4 and/or the down-regulation IL-6 and/or IL-1β.

A further use is to assess the efficacy of the cell to achieve any of the above results as a pre-treatment diagnostic that precedes administering the cells to a subject. Moreover, dosage can depend upon the potency of the cells that are being administered. Accordingly, a pre-treatment diagnostic assay for potency can be useful to determine the dose of the cells initially administered to the patient and, possibly, further administered during treatment based on the real-time assessment of clinical effect.

In a specific embodiment, the pre-treatment diagnostic procedure involves assessing the potency of the cells to up-regulate IL-10 and/or IL-4 and/or down-regulate IL-6 and/or IL-1β.

It is also to be understood that the cells of the invention can be used not only for purposes of treatment, but also research purposes, both in vivo and in vitro to understand the mechanism involved normally and in disease models. In one embodiment, assays, in vivo or in vitro, can be done in the presence of agents known to be involved in the biological process. The effect of those agents can then be assessed. These types of assays could also be used to screen for agents that have an effect on the events that are promoted by the cells of the invention. Accordingly, in one embodiment, one could screen for agents in the disease model that reverse the negative effects and/or promote positive effects. Conversely, one could screen for agents that have negative effects in a non-disease model.

Compositions

The invention is also directed to cell populations with specific potencies for achieving any of the effects described herein. As described above, these populations are established by selecting for cells that have desired potency. These populations are used to make other compositions, for example, a cell bank comprising populations with specific desired potencies and pharmaceutical compositions containing a cell population with a specific desired potency.

In a specific embodiment, the cells have a desired potency to up-regulate IL-10 and/or IL-4. In another specific embodiment, they have the desired potency for down-regulating IL-6 and/or IL-1β.

NON-LIMITING EXAMPLES

Example 1

Intravenous Cell Therapy for Traumatic Brain Injury Preserves the Blood/Brain Barrier Via an Interaction with Splenocytes in a Rat Traumatic Brain Injury Model Summary Recent investigation has shown an interaction between transplanted progenitor cells and resident splenocytes leading to modulation of the immunologic response (Vendrame et al., *Exp Neurol* 199:191-201 (2006)). The inventors hypothesized that the intravenous injection of a class of primitive non-embryonic progenitor cells (designated "MAPC") offers neurovascular protection via an interaction with resident splenocytes leading to blood brain barrier (BBB) preservation.

Four groups (n=6/group) of rats underwent controlled cortical impact (CCI) injury (3 groups) or sham injury (1 group). MAPCs were injected via the tail vein at two doses ($2 \times 10^6$ MAPC/kg or $10 \times 10^6$ MAPC/kg) 2 and 24 hours after injury. BBB permeability was assessed by measuring Evans blue dye extravasation. Splenic mass was measured followed by splenocyte characterization, cell cycle analysis, and anti-inflammatory cytokine measurements. Vascular architecture was determined by immunohistochemistry.

CCI injury decreased splenic mass and increased BBB permeability. Intravenous MAPC therapy preserved splenic mass and returned BBB permeability towards sham levels. Splenocyte characterization showed an increase in the number and proliferative rate of $CD4^+$ T-cells as well as an increase in IL-4 and IL-10 production in stimulated splenocytes isolated from the MAPC treatment groups. Immunohistochemistry demonstrated stabilization of the vascular architecture in the peri-lesion area.

TBI causes a reduction in splenic mass that correlates with an increase in circulating immunologic cells leading to increased BBB permeability. The intravenous injection of MAPC preserves splenic mass and the BBB. Furthermore, the co-localization of transplanted MAPC and resident CD4+ splenocytes is associated with a global increase in IL-4 and IL-10 production and stabilization of the cerebral microvasculature tight junction proteins.

Introduction

The inventors hypothesized that intravenous MAPC injection would preserve (Vendrame et al., *Exp Neurol* 199:191-201 (2006)) the lost splenic mass and potentially increase splenocyte proliferation resulting in production of the anti-inflammatory cytokines such as IL-4 and IL-10. The production of IL-4/IL-10 could modulate the pro-inflammatory response after injury in the direct injury and penumbral regions of the brain leading to preservation of the BBB. To test the hypothesis, a series of in vivo and in vitro experiments were completed to investigate the interaction of intravenous MAPC therapy with splenocytes and their resultant effect on the BBB.

Experimental Designs

In Vivo Designs

Four groups (n=6/group) of normal Sprague-Dawley rats underwent controlled cortical impact (CCI) injury (3 groups) or sham injury (1 group). Clinical grade human MAPC have been previously described (Kovacsovics-Bankowski et al., *Cytotherapy* 10:730-42 (2008) and Kovacsovics-Bankowski et al., *Cell Immunol* 255:55-60 (2009)), and were provided by Athersys. Cells were injected via the tail vein at either of two separate doses ($2 \times 10^6$ MAPC/kg or $10 \times 10^6$ MAPC/kg) at two times, 2 and 24 hours, after injury. 72 hours after injury, Evan's blue dye was injected into the animal via the internal jugular vein. After 1 hour of circulation, the animals were sacrificed with subsequent homogenization of the injured cortical hemisphere and overnight incubation in formamide. Finally, BBB permeability was determined via measurement of Evan's blue absorbance (Pati et al., *Stem Cells and Development* (2010)). After completion of BBB permeability analysis using normal Sprague Dawley rats, a second set of animals was obtained after splenectomy. After adequate recovery from the splenectomy, the above protocol was repeated for BBB permeability analysis.

An additional four groups of normal Sprague Dawley rats (n=12/group) underwent CCI injury and cell injection as described above without Evan's blue perfusion. The animals were sacrificed at 72 hours after injury. Immediately after death, the brains were removed and frozen for immunohistochemistry. Additionally, a splenectomy was performed with subsequent measurement of splenic mass. At this time, the splenocytes were isolated for completion of the in vitro experiments described below. Four groups of Sprague Dawley rats status post splenectomy (n=3/group) underwent CCI injury and cell injection as described with subsequent brain harvest for immunohistochemistry.

Finally, in order to track MAPC in vivo, four groups of normal rats (n=2/group) underwent CCI or sham injury. Next, the treatment groups were injected with quantum dot labeled MAPC 2 and 24 hours after injury with animal sacrifice 6 hours after the second cell dosage. The spleens were removed and a fluorescent scan was completed to track any MAPC located in the spleen followed by immunohistochemistry to observe splenic structure and MAPC location.

In Vitro Designs

After measurement of splenic mass, the splenocytes were harvested for analysis. First, the splenocyte populations were characterized via flow cytometric based measurement of neutrophil (CD11/CD18b) (n=3/group), monocyte (CD200) (n=3/group), and T-cell populations (CD3/CD4/CD8) (n=9/group). Next, the splenocytes were cultured for 72 hours and stimulated with concanavalin A. After incubation, $CD3^+/CD4^+$ T-cell proliferation was analyzed using a BRDU kit to evaluate the percentage of splenocytes in the S phase of the cell cycle (n=6/group). Finally, using a flow cytometric-based bead array, the production of the anti inflammatory cytokines IL-4 and IL-10 was measured (n=6/group).

After completion of the splenocyte assays, the fresh frozen brain samples were cut into 20 μm sections. The structural correlate to BBB integrity was assessed using an antibody for the tight junction protein occludin.

Results

Blood Brain Barrier (BBB) Permeability

BBB permeability measurement was completed using Evan's blue dye in both normal rats and rats after splenectomy (n=6/group). FIG. 1 shows the mean absorbance (nm) normalized to tissue weight (grams) derived from homogenized cortical tissue derived from the hemisphere ipsilateral to the CCI injury. Normal rats without splenectomy show a significant increase in BBB permeability after injury (p=0.0001) that is reversed by the intravenous injection of MAPC. Furthermore, the rats' status post-splenectomy fail to show such a dramatic increase in permeability. It is important to note that the MAPC-mediated effect is dependent upon an intact spleen and is equivalent for both the lower and higher cell dosage.

Tight Junction Immunohistochemistry

Figure 2:
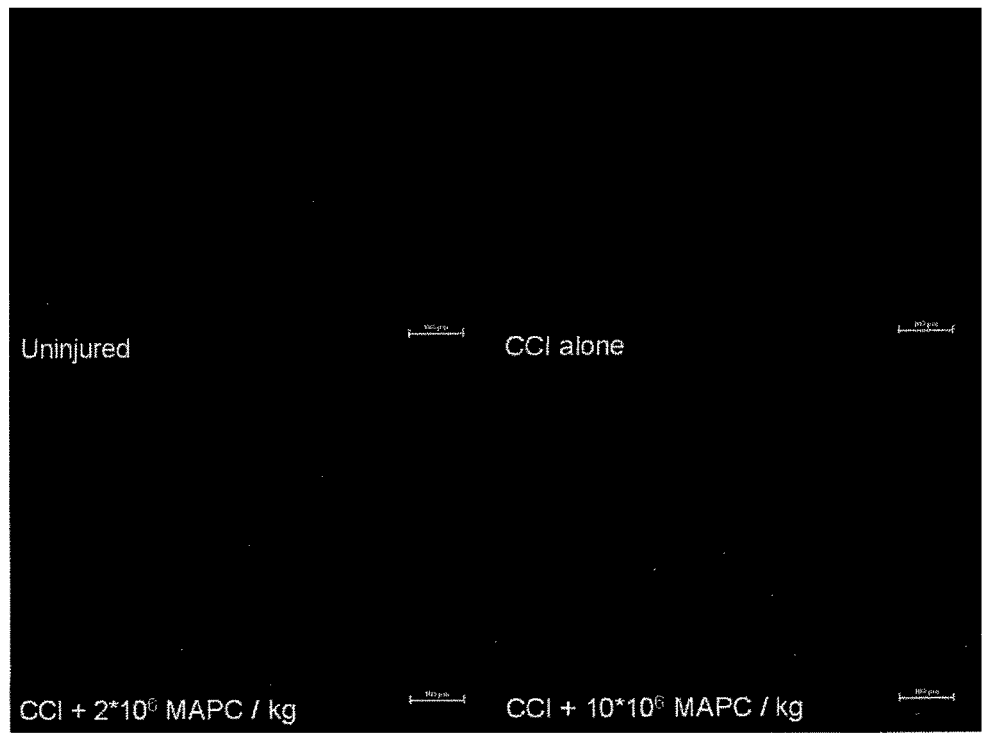
FIG. 2—Immunohistochemistry of the vascular architecture in the pen-lesion area of normal rats. Immunohistochemistry analyzing the tight junction protein occludin (FITC/green) with double stained nuclei (DAPI/blue). Observation of the slides shows a clear decrease in occludin staining in the CCI injury control animals when compared to the uninjured control group. Additionally, there appears to be an increase in occludin observed for both treatment groups. Close observation of the CCI+2×10$^6$ MAPC/kg treatment group shows an increased occludin signal; however, the vasculature appears to be shorter and more disorganized than the uninjured controls. Furthermore, analysis of the CCI+10×10$^6$ MAPC/kg treatment group shows both increased occluding staining and a larger population of more lengthy and organized vessels. (Pictures are 10× with bars measuring 100 μm).

BBB integrity was further examined by immunostaining for the tight junction protein, occludin, and visualization with fluorescent microscopy (DAPI blue for nuclei and FITC green for occludin). FIG. 2 shows representative images from each group for normal rats (uninjured, CCI injury alone, CCI+$2\times10^6$ MAPC/kg, and CCI+$10\times10^6$ MAPC/kg). There is a qualitative decrease in occludin staining in the CCI injury control animals when compared to the uninjured control group. Additionally, there is a qualitative increase in occludin observed for both treatment groups. Close observation of the CCI+$2\times10^6$ MAPC/kg treatment group shows an increased occludin signal likely due to decreased breakdown of the tight junctions; however, the vasculature appears to be shorter and more disorganized than in the sham animals. Furthermore, qualitative analysis of the CCI+$10\times10^6$ MAPC/kg treatment groups suggests both increased occludin staining and a larger population of more lengthy and organized vessels.

Figure 3:
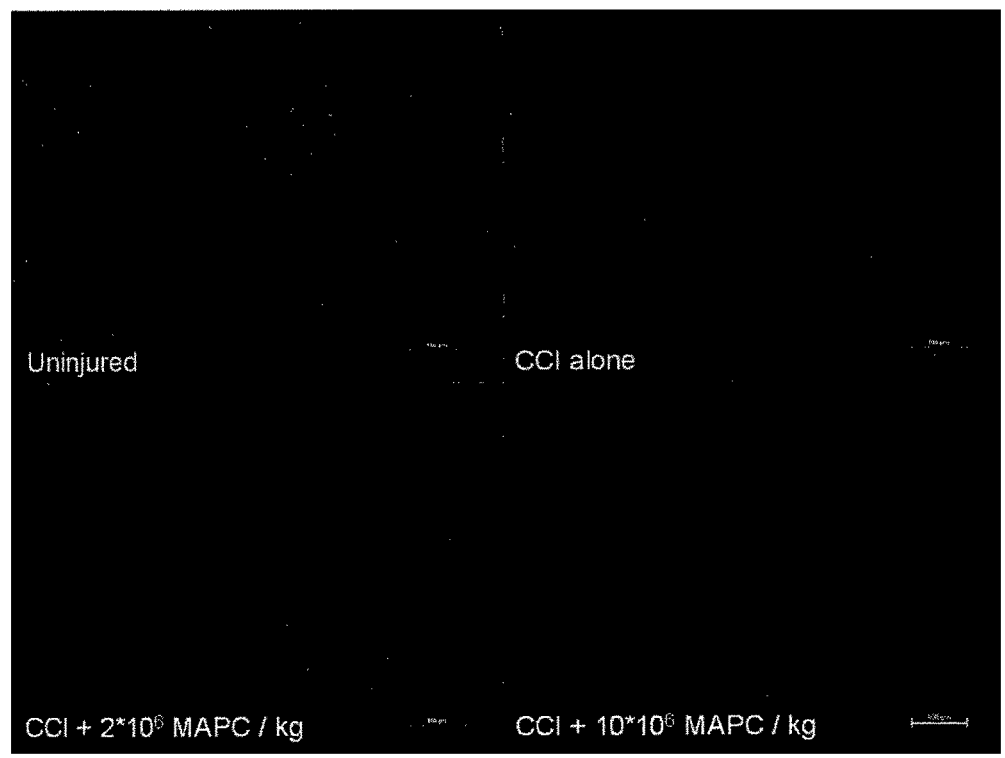
FIG. 3—Immunohistochemistry of the vascular architecture in the pen-lesion area of rats after splenectomy. Immunohistochemistry analyzing the tight junction protein occludin (FITC/green) with double stained nuclei (DAPI/blue) of rats status post splenectomy. Observation of the slides shows a slight decrease in occludin staining in the CCI injury control and treatment animals when compared to the uninjured control group. The observed difference is less pronounced than in the normal rats. Additionally, no clear difference in occludin staining is observed between the CCI injury alone and treatment groups. (Pictures are 10× with bars measuring 100 μm).

Analysis of the tight junction protein, occludin, was repeated with the rats' status post-splenectomy and representative images are shown in FIG. 3. Observation of the images shows a slight decrease in occludin staining in the CCI injury control and treatment animals when compared to the uninjured control group. The observed difference is less pronounced than in the normal rats. Additionally, no clear difference in occludin staining is observed between the CCI injury alone and treatment groups.

Splenic Mass

Figure 4:
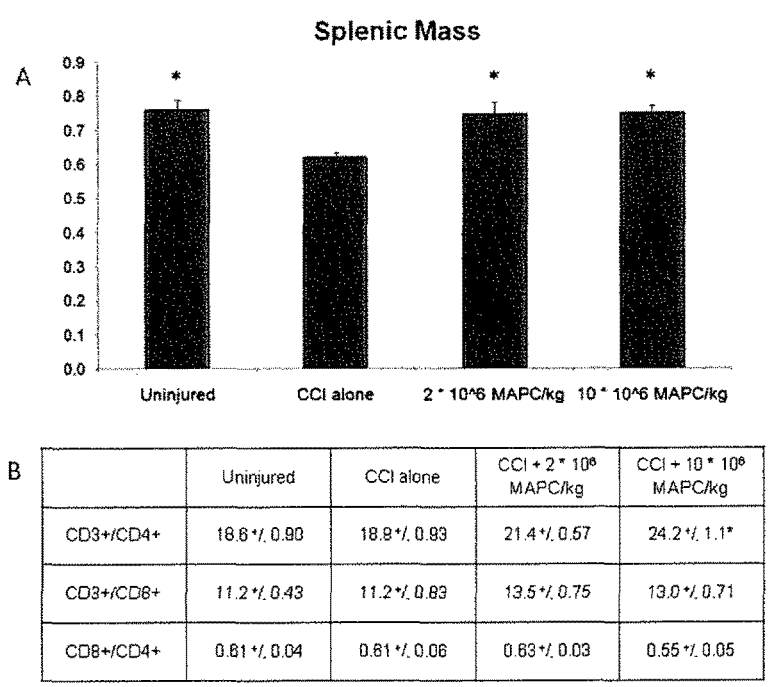
FIG. 4—Mass of spleens and splenocyte T cell characterization recorded 72 hours after cortical injury. A) Mass of spleens (grams) recorded 72 hours after CCI injury (n=12/group). B) The percentage of splenocytes that were CD3$^+$/CD4$^+$ or CD3$^+$/CD8$^+$ double positive as well as the CD8$^+$/CD4$^+$ ratio (n=9/group). A trend towards increased CD3$^+$/CD4$^+$ double positive cells was observed that reaches significance at the higher (10×10$^6$ MAPC/kg) cell dosage (p<0.001). * indicates statistical significance compared to CCI injury alone control sample (ANOVA with Tukey Kramer post hoc p<0.05).

Seventy two hours after CCI injury, normal rats (n=12/group) were sacrificed with subsequent measurement of splenic weight. FIG. 4A shows splenic mass measured 72 hours after cortical injury. A significant decrease in mass (p=0.002) was observed in the CCI alone control animals (0.62±0.014 grams) when compared to uninjured controls (0.76±0.029 grams). In addition, the splenic mass was preserved by injection of both $2\times10^6$ MAPC/kg (0.74±0.037 grams) and $10\times10^6$ MAPC/kg (0.75±0.026 grams).

In Vivo MAPC Tracking

In order to ensure that MAPC were bypassing the pulmonary microvasculature and reaching the spleen, quantum dot labeled-MAPCs were injected. Six hours after the second cell dose a splenectomy was performed. FIG. 5A shows a fluorescent scan of both total splenic body and splenic cross section to display the amount of MAPC located in the spleen. As expected, no signal (blue) was observed in the CCI alone control group. Further observation showed increasing signal (yellow representing a moderate signal and red representing a high signal level) for both of the treatment groups indicating an increasing number of MAPC located within the splenic tissue as a function of increasing dose.

Figure 5:
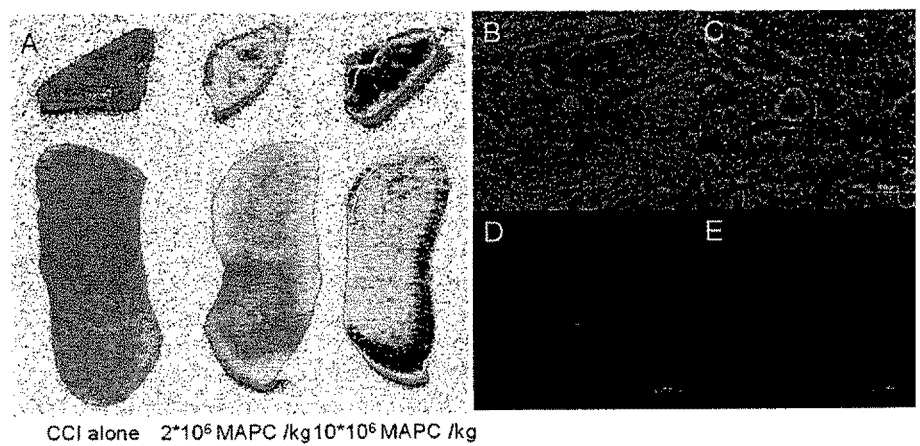
FIG. 5—In vivo tracking of quantum dot labeled MAPC after intervenous injection showing accumulation of cells in the spleen. Fluorescent scans (A), hematoxylin and eosin (H & E) structural stains (B-C), and immuno histochemistry (D-E) of quantum dot labeled (green) MAPCs located in splenic tissue. (A): Fluorescent scan of both total splenic body and splenic cross section to display the amount of MAPCs located in the spleen. As expected no signal (blue) is observed in the CCI alone control group. Further observation shows increasing signal (yellow representing a moderate signal and red representing a high level of signal) for both of the treatment groups indicating an increasing number of MAPCs located in within the splenic tissue. (B-C): H & E stain of a splenic cross section. Both images show a perforating arteriole within the splenic tissue. It is important to note that the splenic white pulp (areas rich in lymphocytes) are located around the arterioles. (D-E) shows several quantum dot labeled MAPCs (labeled green) located within the white pulp in close approximation with the blood vessel allowing for interaction with the resident splenic lymphocyte population. (B/D are 10× with bars measuring 100 μm) (C/E are 20× with bars measuring 100 μm).

To further investigate the location of MAPC within the splenic tissue, structural staining and immunofluorescence were completed as previously described. FIG. 5 B-C shows a structural H & E stain of a splenic cross section. Both images show a perforating arteriole within the splenic tissue. It is important to note that the splenic white pulp (areas rich in lymphocytes) are located around the arterioles. Furthermore, FIG. 5 D-E shows quantum dot labeled-MAPC (labeled green) located within the white pulp in close approximation with the blood vessel, suggesting an interaction with the resident splenic lymphocyte population.

Splenocyte Characterization

Splenocytes were isolated 72 hours after CCI injury for characterization using flow cytometry (n=9/group). FIG. 4B outlines the percentage of splenocytes that were $CD3^+/CD4^+$ or $CD3^+/CD8^+$ double positive as well as the $CD8^+/CD4^+$ ratio. A trend towards increased $CD3^+/CD4^+$ double positive cells was observed at the $2\times10^6$ MAPC/kg cell dosage that reaches significance at the higher ($10\times10^6$ MAPC/kg) cell dosage (p<0.001). In addition a trend towards an increase in $CD3^+/CD8^+$ double positive cells is observed (p=0.10). Furthermore, no difference in the $CD8^+/CD4^+$ ratio was observed.

In addition to T cell characterization, the splenocytes were stained with CD200 and CD11/CD18b to measure the monocyte and neutrophil populations, respectively (n=3/group). No significant differences were noted between the groups (data not shown).

$CD4^+$ T-Cell Proliferation

To further investigate the significant increase in $CD4^+$ T-cells, cell cycle analysis was completed using a flow cytometric based BRDU assay kit (n=6/group). Splenocytes were gated for $CD4^+$ and then the percentage of cells in S phase (actively proliferating) was measured. FIG. 5A shows a decrease in $CD4^+$S phase proliferation observed for the CCI injury alone control animals (27.7±6.6%) compared to the uninjured controls (43.8±1.9%). In addition, the proliferative rate was restored by injection at both $2\times10^6$ MAPC/kg (46.2±2.6%) and $10\times10^6$ MAPC/kg (45.9±3.5%) cell dosages (p=0.01).

Anti-Inflammatory Cytokine Production

Subsequently, the potential effect of MAPC therapy on the systemic inflammatory response was tested as splenocytes were isolated and cultured in stimulated growth media as described above. Using a flow cytometry bead-based cytokine array, the production of the anti-inflammatory cytokines IL-4 and IL-10 (pg/ml) was measured and is displayed in FIG. 5B. A trend towards increased IL-4 and IL-10 production is observed for both treatment groups compared to CCI injury alone control animals. This is significant at the higher cell dosage ($10\times10^6$ MAPC/kg) for both IL-4 (p=0.02) and IL-10 (p=0.03) production.

Discussion

Figure 7:
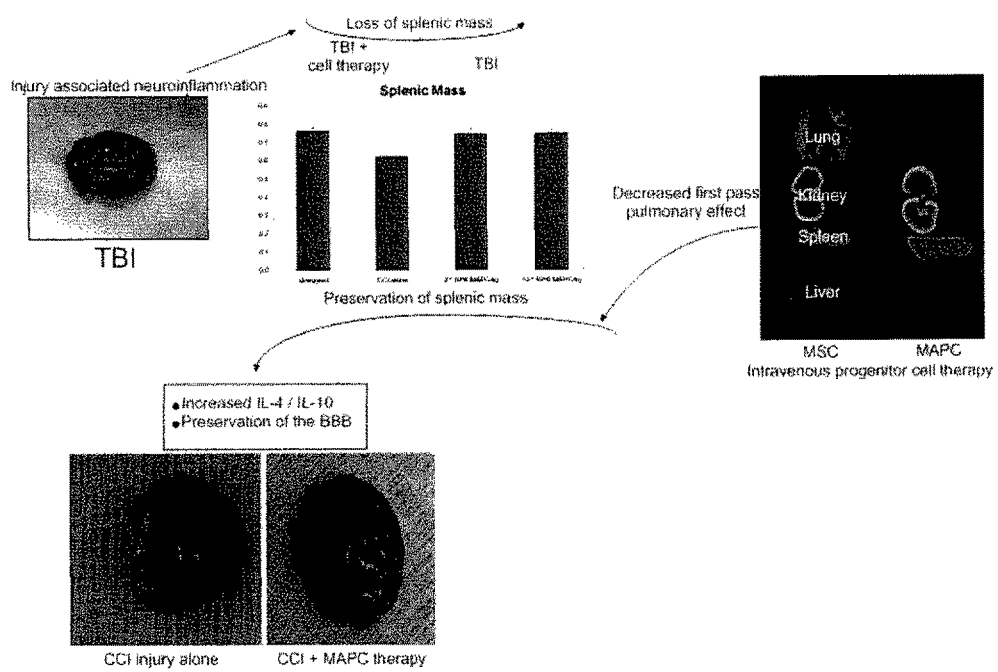
FIG. 7—Mechanism of neurovascular protection after the intravenous injection of MAPC. The data show that CCI injury decreased splenic mass and increased BBB permeability. Intravenous MAPC therapy "rescued" splenic mass and returned BBB permeability towards sham levels at both cell dosages. Splenocytes harvested from the treatment groups showed an increase in IL-4 and IL-10 production.

The data show that CCI injury decreased splenic mass and increased BBB permeability. Intravenous MAPC therapy preserved splenic mass and returned BBB permeability towards sham levels at both cell dosages. The same protocol completed in the rats' status post-splenectomy failed to demonstrate a dramatic increase in BBB permeability with CCI injury and showed no difference between control and cell-treated groups. Therefore, the observed cell benefit required an interaction between injected MAPCs and resident splenocytes. Splenocyte characterization showed an increase in the absolute number and proliferative rate of $CD4^+$ T-cells as well as an increase in IL-4 and IL-10 production in stimulated splenocytes isolated from the MAPC treatment groups. Immunohistochemistry demonstrated stabilization of the vascular architecture in the peri-lesion area. FIG. 7 outlines a proposed mechanism of MAPC therapy leading to preservation of the BBB barrier in TBI.

Using a CCI injury model for TBI creates localized parenchymal inflammation and edema thereby making injury cavity analysis a poor measure of therapeutic efficacy in the acute phase after injury. Therefore, Evan's blue dye extravasation was used to measure BBB permeability at the known temporal peak of cerebral edema development. BBB permeability increased 72 hours after injury in the CCI injury control animals (FIG. 1). Furthermore, the increase in permeability correlates with a significant reduction in splenic mass (FIG. 4A). The intravenous injection of both $2\times10^6$ MAPC/kg $10\times10^6$ MAPC/kg prevents the loss in splenic mass and maintains the integrity of the BBB. The same protocol repeated in animals status post splenectomy failed to show such a dramatic increase in BBB permeability for CCI injury control animals indicating the spleen to be intimately involved in BBB breakdown. In addition, the spleen has to be present in order for the injected progenitor cells to have effect on BBB permeability.

Figure 6:
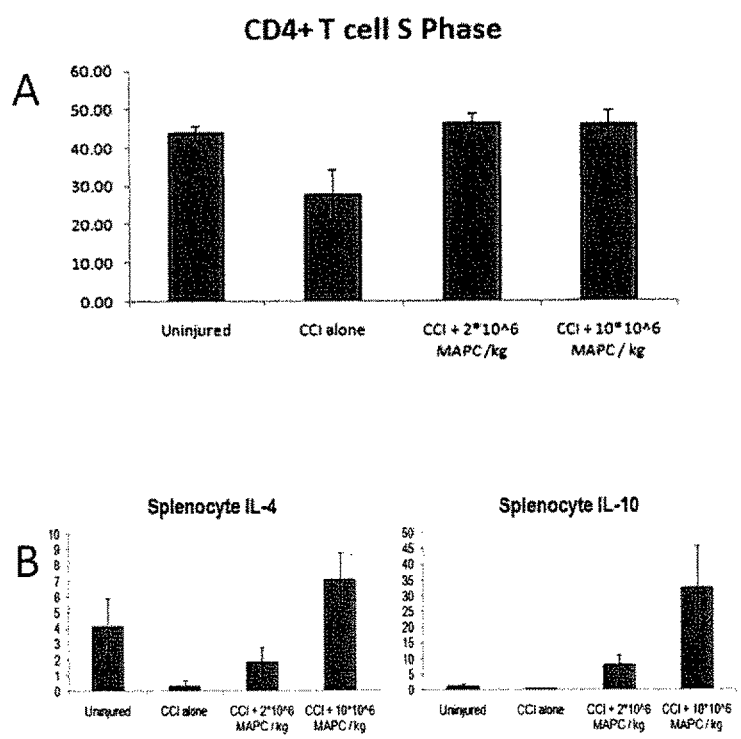
FIG. 6—Splenocyte CD4+ T cell proliferation and anti inflammatory cytokine production. A) Percentage of CD4+ splenocytes (n=6/group) that were in the S phase (actively proliferating). Control animals with CCI injury had a decrease in proliferation that was restored by both treatment doses. B) Anti inflammatory cytokine production (pg/mL) derived from splenocytes after 72 hours of expansion in stimulated (2 μg/mL) concanavalin A growth media. A trend towards increased cytokine production is observed for both cell doses. The trend reaches significance at the higher dose ($10 \times 10^6$ MAPC/kg) for both IL-4 (p=0.02) and IL-10 (p=0.03) production. * indicates statistical significance compared to CCI injury alone control sample (ANOVA with Tukey Kramer post hoc, p<0.05).

To further characterize the loss in splenic mass, the inventors completed flow cytometric based immunophenotyping of the cell surface markers, CD3, CD4, and CD8. FIG. 4B outlines a significant increase in the percentage of $CD3^+/CD4^+$ double positive T-cells. In accordance with the observed preservation of splenic mass, an absolute increase in the number of $CD4^+$ T-cells is present in the spleens of treatment animals. Additionally, FIG. 6A shows an increase in actively proliferating $CD4^+$ T-cells in the treatment groups indicating that the progenitor cell/splenocyte interaction is activating the resident T-cells to proliferate accounting for the observed protection of splenic mass.

$CD4^+$ T-cells may differentiate into regulator or effector T-cells that are responsible for many functions including modulation of the immunologic response and the release of anti-inflammatory cytokines. FIG. 6B shows a trend towards increased IL-4 and IL-10 production that reaches significance at the higher MAPC dosage ($10\times10^6$ MAPC/kg). These findings represent a global increase in anti-inflammatory cytokine production that could modulate the immunologic/inflammatory response and modulate the parenchymal and vascular tissue surrounding the area of injury leading to decreased resident endothelial cell and neuronal apoptosis thereby potentially attenuating the deficit observed with TBI.

Immunohistochemical images of the endothelial tight junction protein, occludin, evaluated the integrity of the BBB (FIGS. 2 and 3). Occludin staining decreased in the CCI injury alone control animals. Additionally, the vessels present appear smaller and more disorganized. Occludin staining increased for both MAPC doses with elongation of the vasculature observed for the higher dosage ($10\times10^6$ MAPC/kg). Furthermore, repeat staining with the rats' status post-splenectomy failed to show a qualitative difference in occludin staining when compared to uninjured control animals. This finding correlates well with the BBB permeability assay and further confirms the role of the spleen in the systemic inflammatory and injury response leading to BBB breakdown. Analysis of the cortical sections confirmed that the most significant changes in the cerebral microvasculature occur in close proximity to the injury cavity edge.

Conclusions

The data show that TBI is associated with a reduction in splenic mass that correlates with the release of $CD8^+$ lymphocytes that is associated with increased BBB permeability. The intravenous injection of MAPC preserves the BBB and splenic mass. Furthermore, the interaction between transplanted MAPC and resident $CD4^+$ splenocytes leads to a global increase in IL-4 and IL-10 production that is a potential modulator of the cerebral microvasculature.

A plausible hypothesized mechanism is that MAPC/splenocyte interactions generate anti-inflammatory cytokines and alter the splenocyte efflux in a manner that changes the endogenous cerebral inflammatory response. Overall, the data demonstrate that injected progenitor cells do not need to engraft to produce a significant biological effect. In fact, injected progenitor cells could potentially act as "distant bioreactors" that modulate the systemic immunologic and inflammatory response via interactions with other organ systems such as splenocytes.

Methods

In Vivo Methods

Controlled Cortical Impact Injury

A controlled cortical impact (CCI) device (eCCI Model 6.3; VCU, Richmond, Va.)) was used to administer a unilateral brain injury as described previously (Lighthall, J., *J Neurotrauma* 5:1-15 (1988)). Male rats weighing 225-250 gram were anesthetized with 4% isoflurane and a 1:1 mixture of $N_2O/O_2$ and the head was mounted in a stereotactic frame. Animals received a single impact of 3.1-mm depth of deformation with an impact velocity of 5.8 msec and a dwell time of 150 msec (moderate-to-severe injury) using a 6-mm diameter impactor tip, making the impact to the parietal association cortex. Sham injuries were performed by anesthetizing the animals, making the midline incision, and separating the skin, connective tissue, and aponeurosis from the cranium. The incision was then closed (Harting et al., *Surgery* 144:803-13 (2008)).

Preparation and Intravenous Injection of MAPC

MAPC were obtained from Athersys, Inc. (Cleveland, Ohio) and stored in liquid nitrogen. Prior to injection, the MAPC were thawed and suspended in phosphate buffered saline (PBS) vehicle at a concentration of $2\times10^6$ cells/mL Cells were counted and checked for viability via Trypan blue exclusion. Immediately prior to intravenous injection, MAPC were titrated gently 8-10 times to ensure a homogeneous mixture of cells. MAPC were injected at both 2 and 24 hours after CCI injury at 2 different dosages (CCI+$2\times10^6$ MAPC/kg, and CCI+$10\times10^6$ MAPC/kg). Therefore, each treatment animal received 2 separate doses of their assigned MAPC concentration. CCI injury control animals received PBS vehicle injection alone at the designated time points.

Evan's Blue BBB Permeability Analysis

Seventy two hours after CCI injury, the rats were anesthetized as described above, and 1 mL (4 cc/kg) of 3% Evan's blue dye in PBS was injected via direct cannulation of the right internal jugular vein. The animals were allowed to recover for 60 minutes to allow for perfusion of the dye. After this time, the animals were sacrificed via right atrial puncture and perfused with 4% paraformaldehyde. Next, the animals were decapitated followed by brain extraction. The cerebellum was dissected away from the rest of the cortical tissue. The brain was divided through the midline and the mass of each hemisphere (ipsilateral to injury and contralateral to injury) was measured for normalization. Subsequently, each hemisphere was allowed to incubate overnight in 5 mL of formamide (Sigma Aldrich, St. Louis, Mo.) at 50 degrees centigrade to allow for dye extraction. After centrifugation, 100 µL of the supernatant from each sample was transferred to a 96 well plate (in triplicate) and absorbance was measured at 620 nm using the VersaMax plate reader (Molecular Devices Inc., Sunnyvale, Calif.). All values were normalized to hemisphere weight.

Cortical Immunohistochemistry

Seventy two hours after CCI injury, 4 groups (uninjured, CCI injury alone, CCI injury+$2\times10^6$ MAPC/kg, and CCI injury+$10\times10^6$ MAPC/kg) of both normal rats and rats after splenectomy were sacrificed followed quickly by decapitation. The brains were extracted and both hemispheres (ipsilateral and contralateral to injury) were isolated. The tissue samples were then quickly placed into pre-cooled 2-methylbutane for flash freezing. The samples were transferred to dry ice and stored at −80 degrees centigrade until the tissue was sectioned.

Next the tissue samples were placed in Optimal Cutting Temperature compound (Sakura Finetek, Torrance, Calif.) and 20 µm cryosections were made through the direct injury area. Direct injury to the vascular architecture was evaluated via staining with an antibody for the tight junction protein occludin (1:150 dilution, Invitrogen, Carlsbad, Calif.) and appropriate FITC conjugated secondary antibody (1:200 dilution, Invitrogen, Carlsbad, Calif.). After all antibody staining, the tissue sections were counterstained with 4'6-diamidino-2-phenylindole (DAPI) (Invitrogen, Carlsbad, Calif.) for nuclear staining and visualized with fluorescent microscopy.

Splenic Immunohistochemistry

In order to track MAPC in vivo, 4 groups of normal rats (uninjured, CCI injury alone, CCI injury+$2\times10^6$ MAPC/kg, and CCI injury+$10\times10^6$ MAPC/kg) underwent either sham injury or CCI injury. Next, the two treatment groups received quantum dot per manufacturer's protocol (QDOT, Qtracker cell labeling kit 525 and 800, Invitrogen, Inc., Carlsbad, Calif.) labeled MAPC injections 2 and 24 hours after CCI injury. Six hours after the second QDOT labeled MAPC dosage, the animals were sacrificed and the spleens removed. Next, the spleens were placed on a fluorescent scanner (Odyssey Imaging System, Licor Inc., Lincoln, Nebr.) to localize QDOT labeled MAPC. After the scan was completed, the tissue samples were then quickly placed into pre-cooled 2-methylbutane for flash freezing. The samples were transferred to dry ice and stored at −80 degrees centigrade until use.

Next the tissue samples were placed in Optimal Cutting Temperature compound (Sakura Finetek, Torrance, Calif.) and 10 µm cryosections were made through the spleens. The tissue sections were stained with 4'6-diamidino-2-phenylindole (DAPI) (Invitrogen, Carlsbad, Calif.) for nuclear staining and both the QDOT labeled MAPC and splenocytes were visualized with fluorescent microscopy. Furthermore, hematoxylin and eosin staining (Sigma Aldrich, Inc, St. Louis, Mo.) was completed per manufacturer's protocol to evaluate splenic architecture.

In Vitro

Splenocyte Isolation and Culture

Seventy two hours after injury, the normal animals underwent splenectomy with measurement of splenic mass. Next, the spleens were morselized using a razor blade, washed with basic media (10% FBS and 1% penicillin/streptomycin in RPMI), crushed, and filtered through a 100 µm filter. The effluent sample from the filter was gently titrated 8-10 times and subsequently filtered through a 40 µm filter to remove any remaining connective tissue. The samples were centrifuged at 1000 g for 3 minutes. Next the supernatant solutions were removed and the samples were suspended in 3 mL of red blood cell lysis buffer (Qiagen Sciences, Valencia, Calif.) and allowed to incubate on ice for 5 minutes. Subsequently, the samples were washed twice with basic media and centrifuged using the aforementioned settings. The splenocytes were counted and checked for viability via Trypan blue exclusion. Splenocytes cultured at a density of $7.5\times10^5$ cells/mL were then allowed to expand for 72 hours in growth media (10% FBS, 1% RPMI with vitamins, 1% sodium pyruvate, 0.09% 2-mercaptoethanol, and 1% penicillin/streptomycin in RPMI) stimulated with 2 µg concanavalin A.

Splenocyte Characterization

The isolated splenocytes were analyzed with flow cytometry (LSR II, BD Biosciences, San Jose, Calif.) to determine the monocyte, neutrophil, and T-cell populations. Monocytes and neutrophils were measured using antibodies to CD200 (Abcam, Cambridge, Mass.) and CD11b/CD18 (Abcam, Cambridge, Mass.), respectively. The splenocyte T-cell populations were labeled using CD3, CD4, and CD8 antibodies (Abcam, Cambridge, Mass.). All staining was completed in accordance with manufacturer's suggested protocol. Of note, the T-cell populations of interest were $CD3^+/CD4^+$ and $CD3^+/CD8^+$. There were 10,000 events for each gated cell population.

Proliferation Assay

The percentage of $CD4^+$ splenocytes actively proliferating (S phase) after culture in stimulated growth media was measured using Click-iT™ EdU Flow Cytometry Assay Kit (Invitrogen, Carlsbad, Calif.). The manufacturer's suggested protocol was followed. Briefly, splenocytes were cultured for 72 hours as previously described in growth media stimulated with 2 µg concanavalin A at a density of $7.5\times10^5$ cells/mL. At this point 20 mM of EdU was added and allowed to incubate for 1 hour. Next, the cells were washed with 4% bovine serum in DMEM (4% FBS) and CD4-PE (Biolegend Inc., San Diego, Calif.) was added to gate the T-cell population of interest. After 30 minutes of incubation, the cells were washed and fixed with 4% paraformaldehyde. Cells were permeabilized using Triton-X100 and then the anti-EdU antibody "cocktail" provided by the manufacturer was added. Finally, the cells were washed followed by the addition of Ribonuclease and CellCycle488-Red stain to analyze DNA content. We gated on the CD4+ cells and collected 10,000 events per analysis.

Splenocyte Cytokine Production

After culture in stimulated growth media, production of the anti-inflammatory cytokines IL-4 and IL-10 was quantified by flow cytometry using a BD Cytometric Bead Array flex set (BD Biosciences, San Jose, Calif.) following manufacturer's suggested protocol. A BD LSR II flow cytometer containing the FCAP Array™ software was used to analyze our samples.

Data Analysis

Unless otherwise indicated, all values are represented as mean±SEM. Values were compared using analysis of variance (ANOVA) with a post-hoc Tukey analysis. A p value of ≤0.05 was used to denote statistical significance.

Example 2

Figure 8:
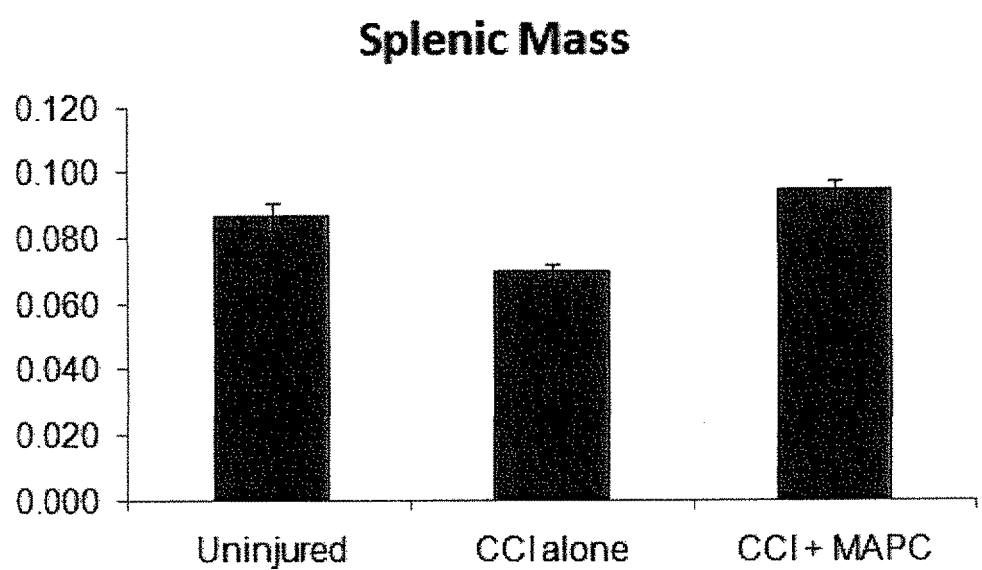
FIG. 8—Splenic mass after cortical injury in mice. The splenic mass was recorded 72 hours after CCI injury.

Intravenous Cell Therapy for Traumatic Brain Injury Preserves the Blood/Brain Barrier Via an Interaction with Splenocytes in a Mouse Traumatic Brain Injury Model Splenic Mass After CCI injury, normal mice were sacrificed with subsequent measurement of splenic weight. FIG. 8 shows splenic mass measured 72 hours after cortical injury. A significant decrease in mass was observed in the CCI alone control animals when compared to uninjured controls. In addition, the splenic mass was preserved by injection of MAPC. The results are presented in FIG. 8.

Blood/Brain Barrier Permeability

Figure 9:
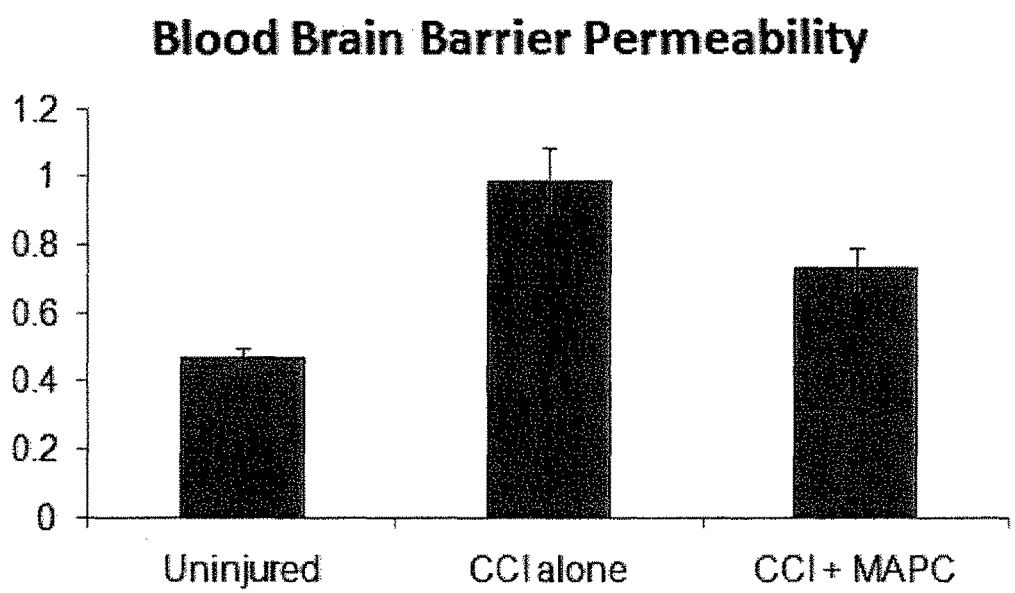
FIG. 9—Blood brain barrier (BBB) permeability measured via Evan's blue extravasation in mouse.

The BBB permeability measurement was completed using Evan's blue dye in both normal mice and mice after splenectomy. FIG. 9 shows the mean of silibance normalized to tissue weight derived from homogenized cortical tissue derived from the hemisphere ipsilateral to the CCI injury. Normal mice without splenectomy show a significant increase in BBB permeability after injury that is reversed by the intravenous injection of MAPC. Normal mice without splenectomy show a significant increase in BBB permeability after injury that is reversed by the intravenous injection of MAPC.

Splenocyte Characteristic

Figure 10:
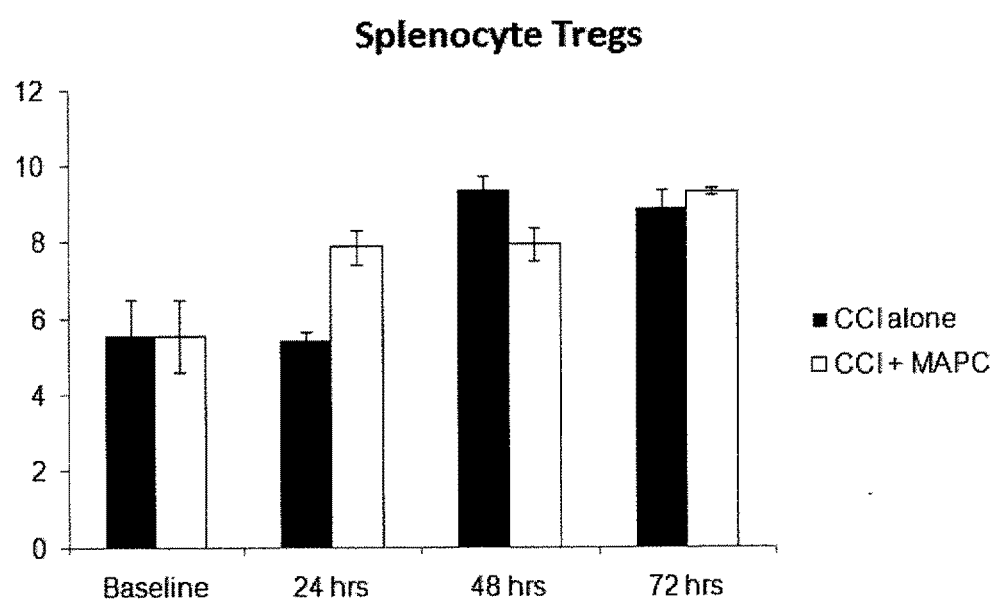
FIG. 10—Splenocyte T-cell characterization.

Splenocytes were isolated 72 hours after CCI injury for characterization using close cytometry. FIG. 10 outlines the percentage of splenocytes that were CD3+/CD4++. A trend towards increased CD3+/CD4− cells was observed at the 24-hour time point in the MAPC-treated mice.

Figure 11:
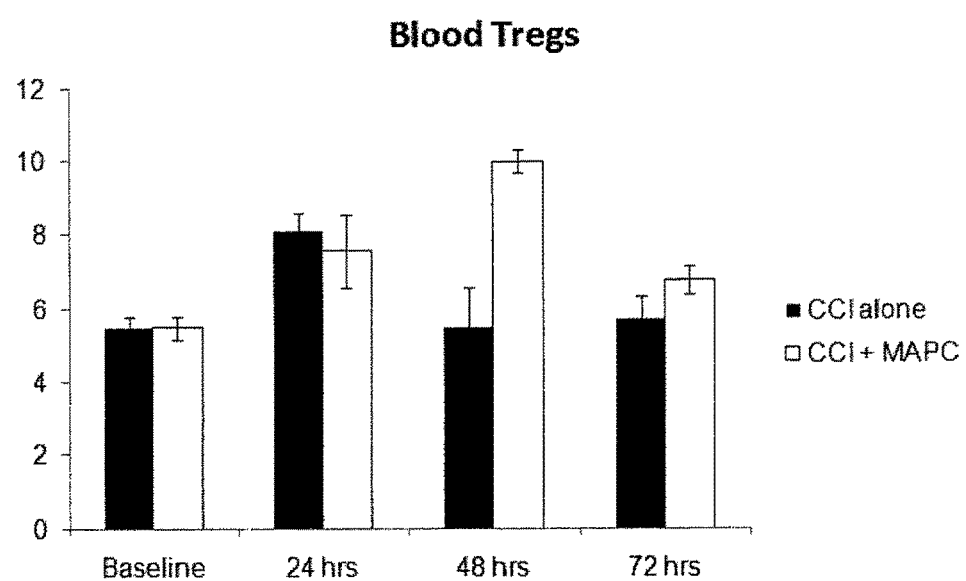
FIG. 11—Peripheral blood T-cell characterization.

FIG. 11 shows that the CD4+ T-cells in peripheral blood were approximately equal at 24 hours in the injured mice treated with and without MAPC. The figure, however, shows a significant increase of the CD4+ T-cells in the peripheral blood at approximately 48 hours post injury in mice treated with MAPC.

Figure 12:
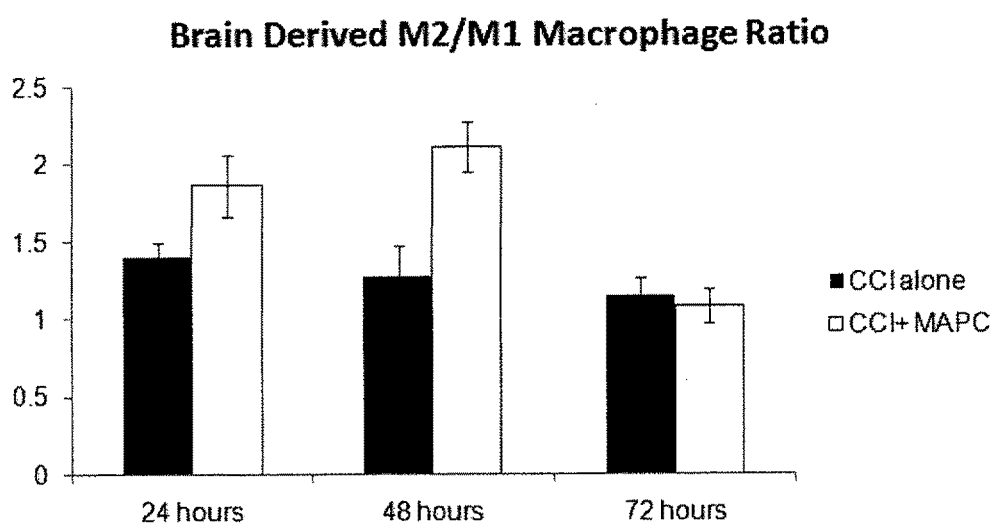
FIG. 12—Brain-derived M1:M2 macrophage ratio following cortical injury in mice.
Figure 13:
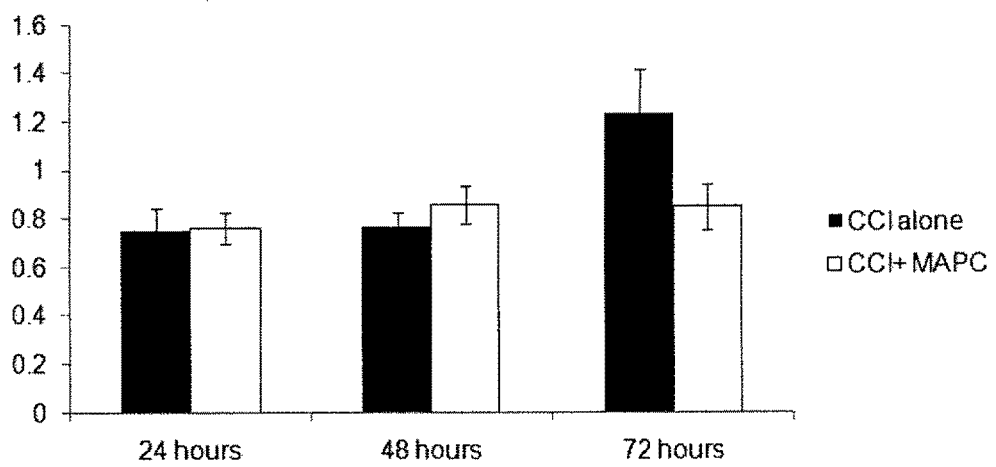
FIG. 13—Blood-derived M1:M2 macrophage ratio following cortical injury in mice.
Figure 14:
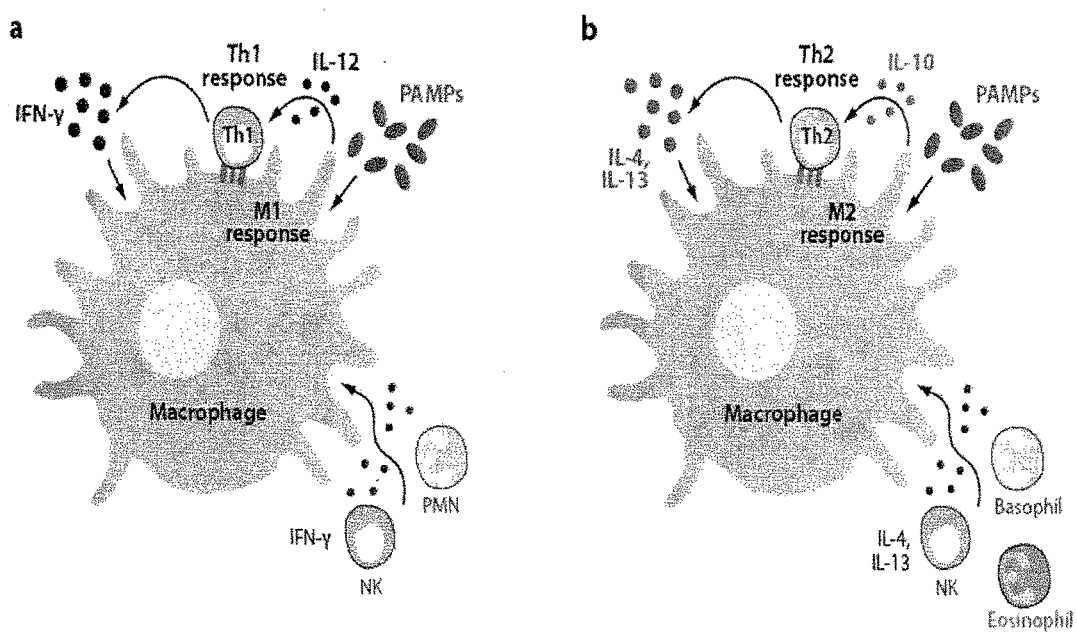
FIG. 14—Anti-inflammatory cytokines must act through other effector cells. This schematic shows M1 classical activation and M2 alternative activation of macrophages. The schematic demonstrates that cytokine and lymphocyte output drives the macrophage phenotype.
Figure 15:
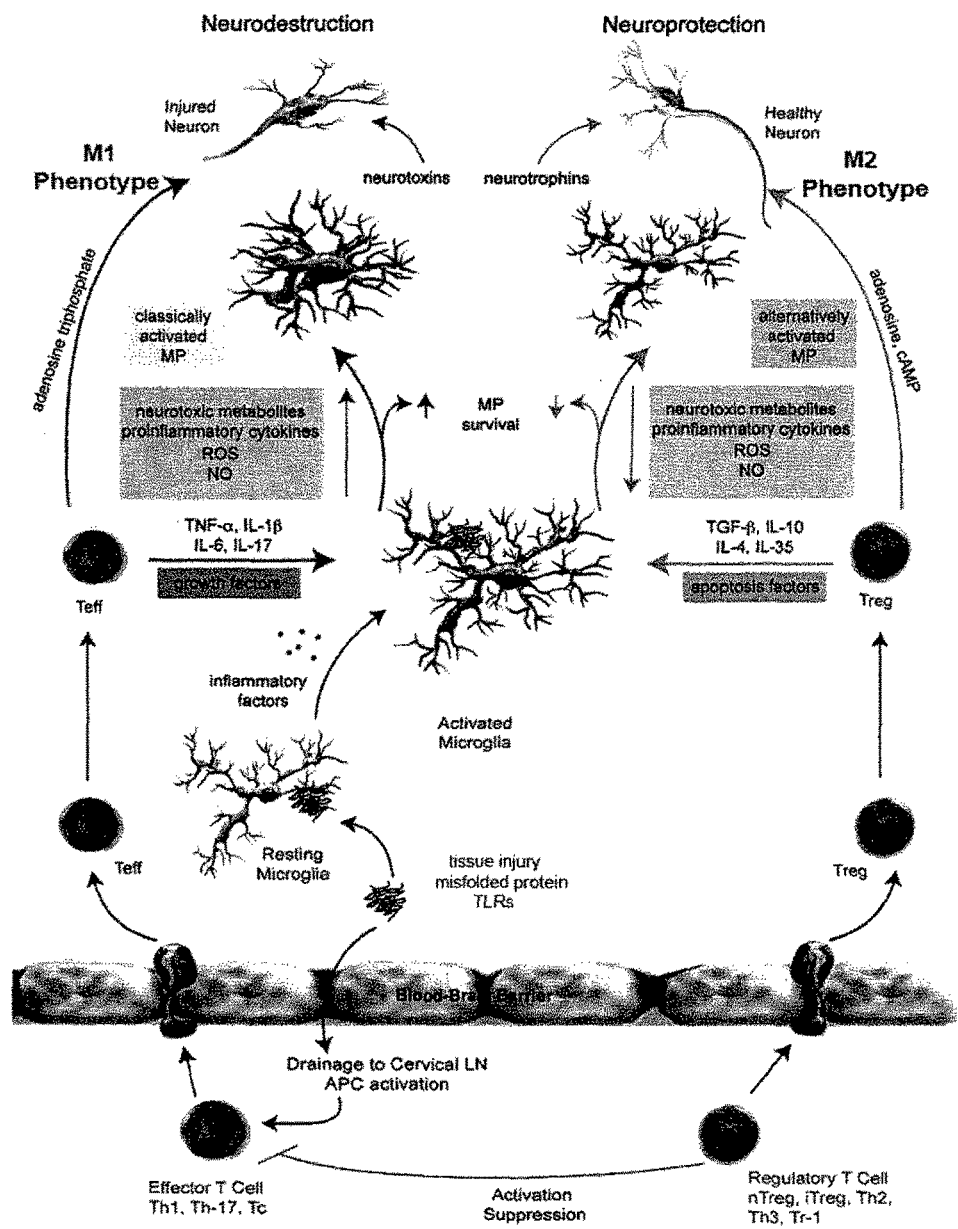
FIG. 15—A more detailed schematic of the pathway toward macrophage M1 phenotype and neurodestruction and M2 phenotype and neuroprotection.
Figure 17:
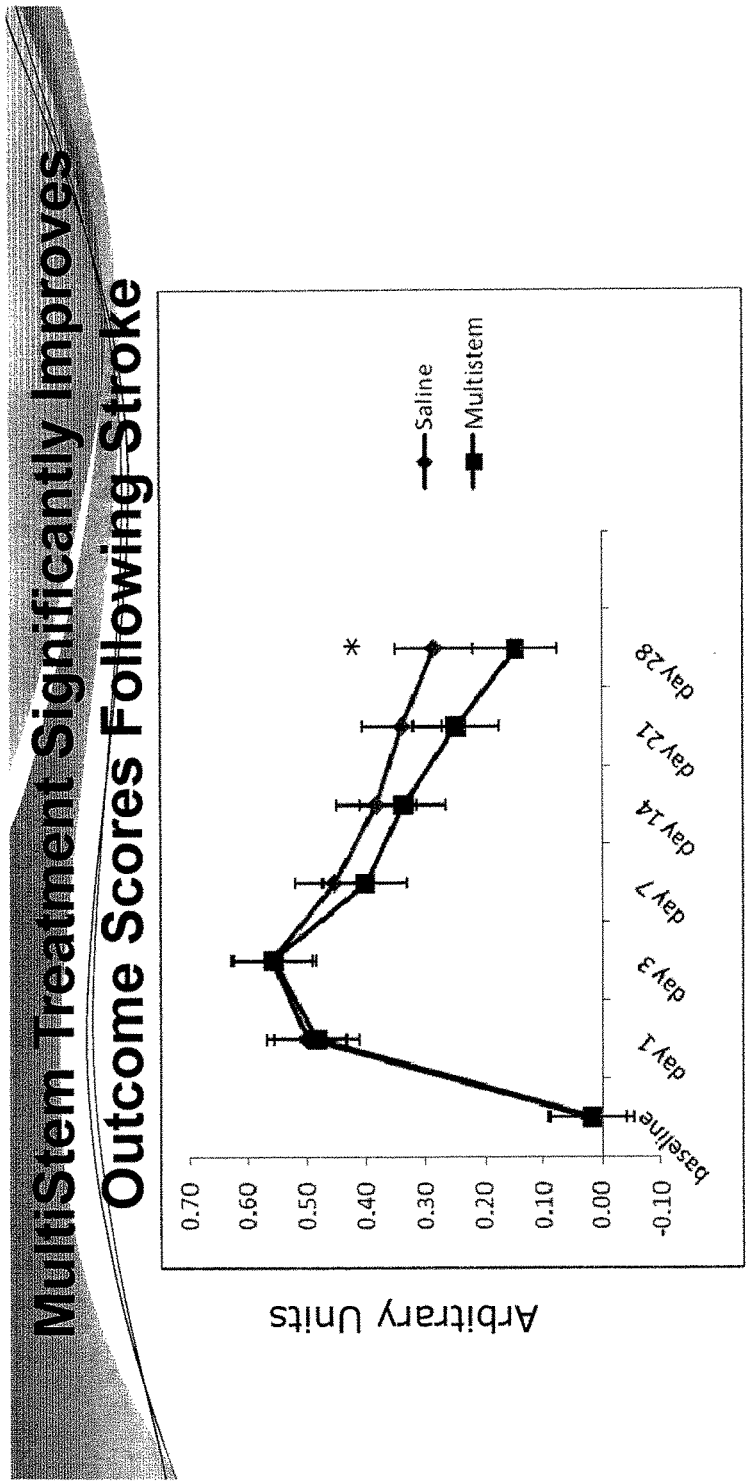
FIG. 17—MultiStem® treatment significantly improves outcome scores following stroke. MultiStem® cells significantly improve the recovery at 28 days after MCAo, compared with saline treatment group. *p<0.05. n=12 each group.
Figure 18:
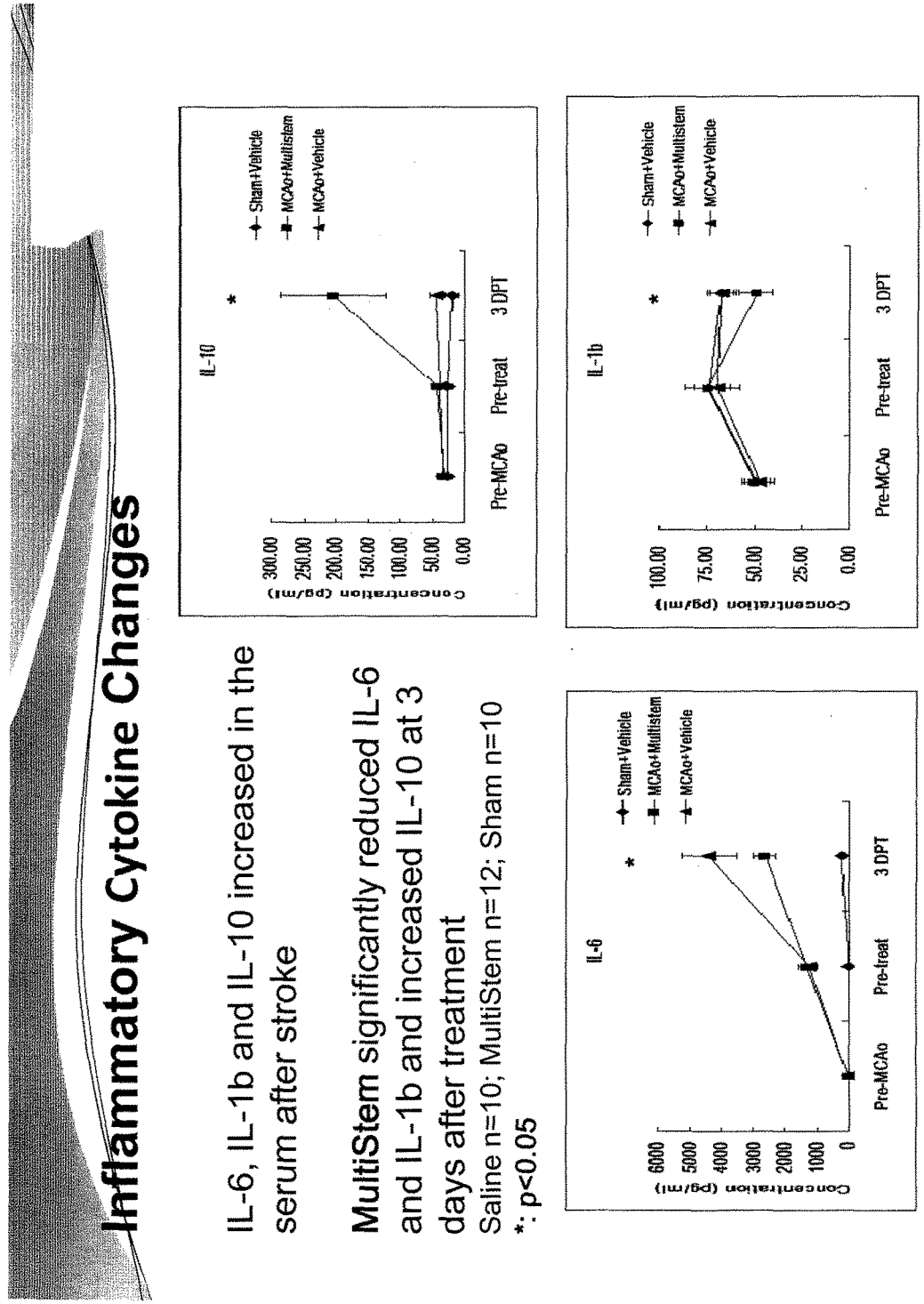
FIG. 18—Inflammatory Cytokine Changes. IL-6, IL-1β, and IL-10 increased in the serum after stroke. MultiStem® significantly reduced IL-6 and IL-1β and increased IL-10 at three days after treatment.
Figure 19:
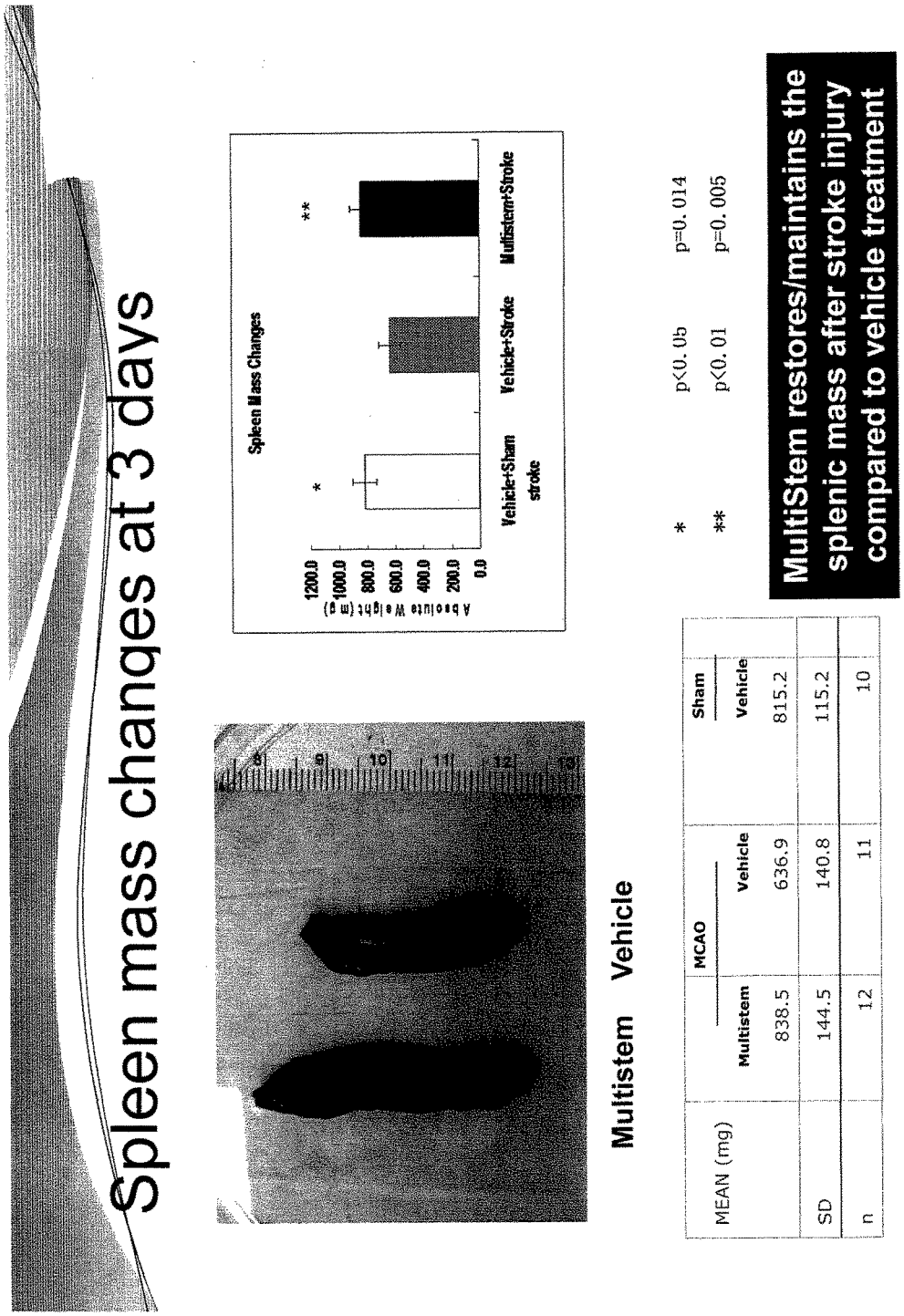
FIG. 19—Spleen mass changes at three days. Multi-Stem® restores/maintains the splenic mass after stroke injury compared to vehicle treatment.
Figure 20:
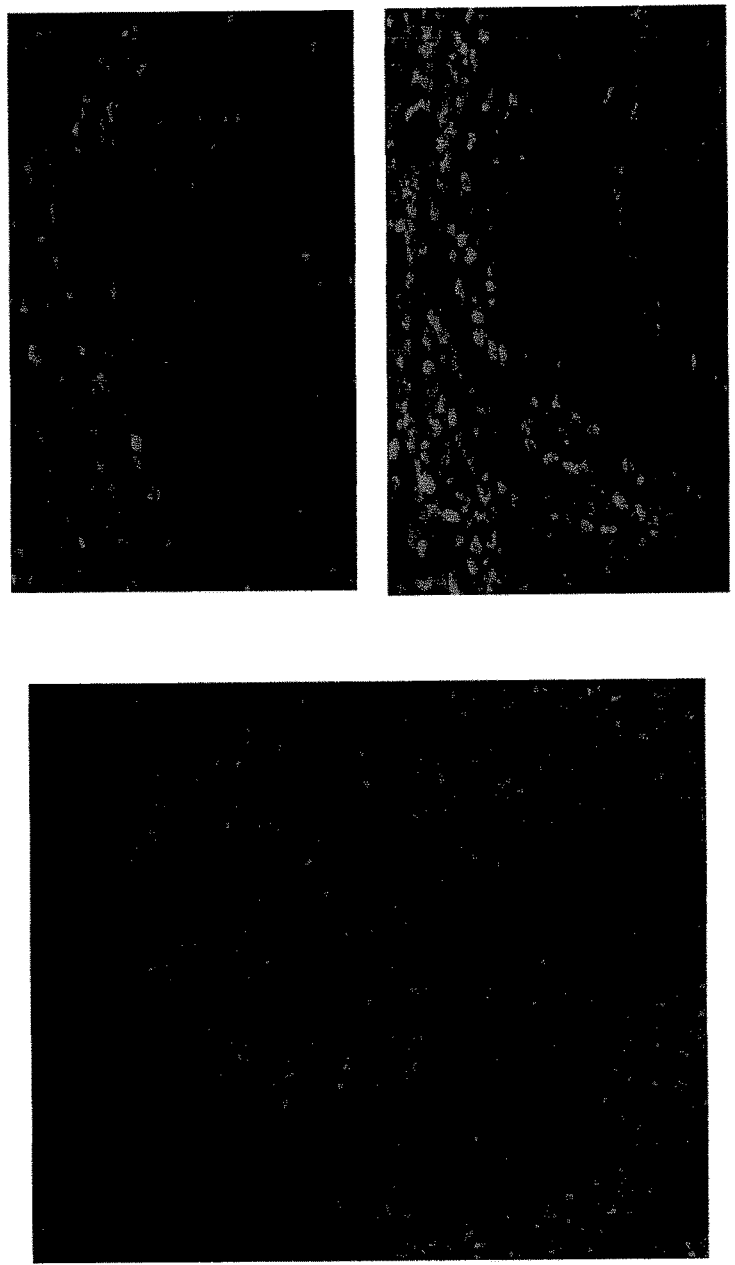
FIG. 20—TUNEL positive cells 72 hours post-treatment. At 72 hours after treatment, TUNEL positive cells were found in the white pulp of the spleen.
Figure 22:
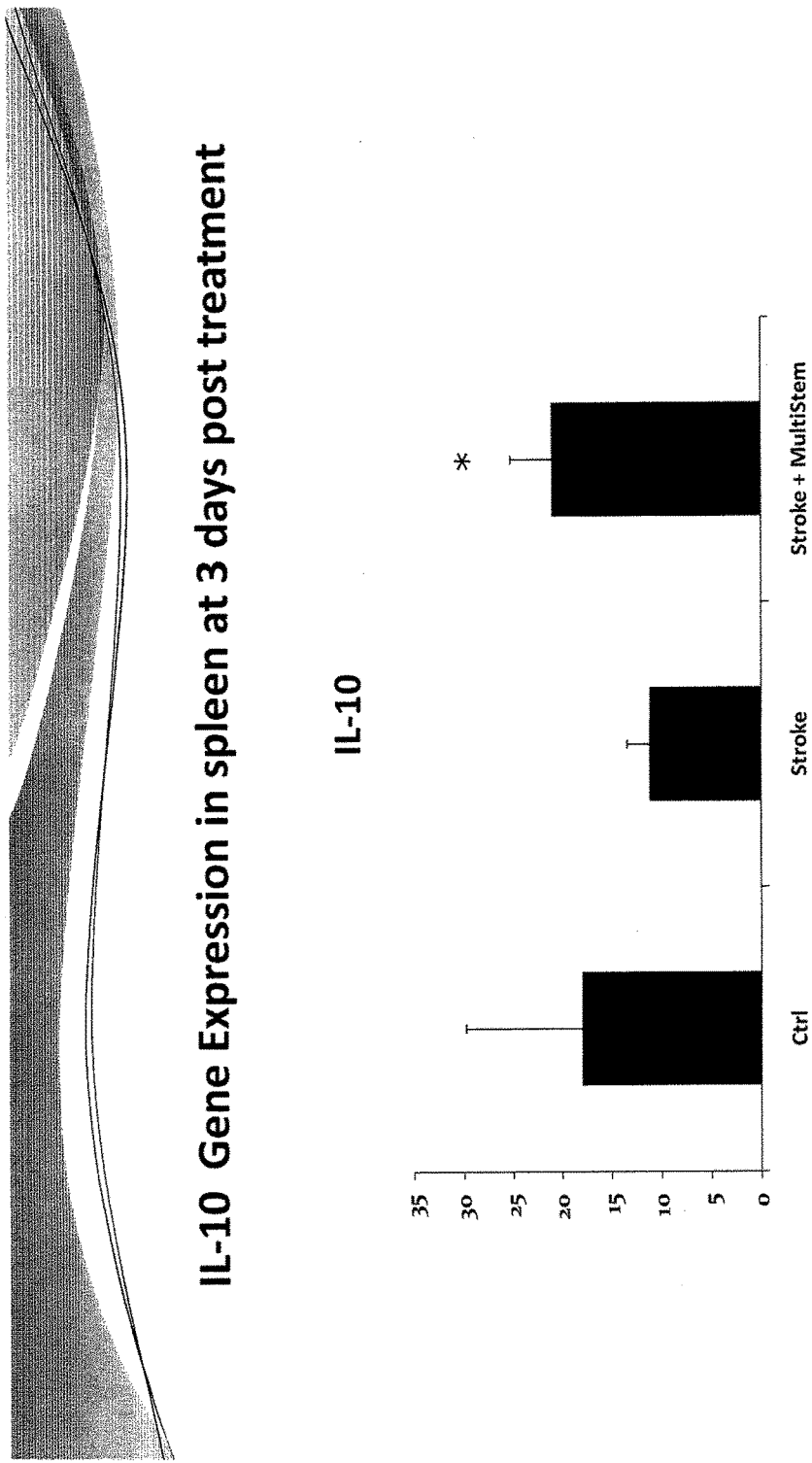
FIG. 22—IL-10 gene expression in spleen at three days post treatment.

Finally, FIGS. 12 and 13 show the effect of MAPC treatment on the brain-derived and blood-derived M2:M1 macrophage ratio, respectively. A significant effect can be seen at 24 hours and 48 hours post-injury.

Example 3

This example shows that human multipotential bone marrow stem cells as described herein exert immunomodulatory effects, prevent splenic contraction, and enhance functional recovery in a rodent model of ischemic stroke. In this particular example, MultiStem® cells were used for conducting the experiment (isolated and cultured under low oxygen, high serum conditions). These experiments were done against the following background considerations: (1) stem cells offer a promising direction to provide a therapy to enhance recovery from a stroke; (2) major mechanism is immunomodulation; and (3) there is an emerging role for the spleen in stroke, namely, that it actively contributes to ongoing injury by releasing inflammatory cytokines and immune cells. The hypotheses for these experiments were that MultiStem® cells would enhance recovery after stroke by immunomodulatory mechanisms involving the spleen.

This example shows that there are inflammatory cytokine changes when MultiStem® is administered in the animal stroke model. Specifically, the example shows that the pro-inflammatory cytokines IL-6 and IL-1β increase in the serum after stroke and that administration of MultiStem® significantly reduces both IL-6 and IL-1β at three days after treatment. The examples also show that the anti-inflammatory cytokine IL-10 increases in serum after stroke and that MultiStem® treatment significantly increases the level of IL-10 three days after treatment.

The Examples show (in FIGS. 16-22) that MultiStem® cells provide an improved clinical outcome in the stroke model.

What is claimed is:

1. A method for obtaining cells that have the ability to (1) preserve splenic mass in an injury, (2) increase splenocyte proliferation in the spleen, (3) increase T-regulatory cells; (4) increase one or more of IL-10 and IL-4, or (5) decrease IL-2 and IL-1β, the method comprising assaying cells for said ability by performing one or more of: (1) an assay of splenic mass in an injury, (2) an assay of splenocyte proliferation in the spleen, (3) an assay of T-regulatory cells (4) an assay of IL-10 and IL-4, and (5) an assay of IL-2 and IL-1β, wherein said cells that are assayed are non-embryonic non-germ cells that express one or more of oct4, telomerase rex-1 or rox-1 and/or can differentiate into cell types of at least two of the endodermal, ectodermal, and mesodermal germ layers.

2. The method of claim 1 wherein the cells express telomerase.

3. The method of claim 1 wherein the cells express oct4.

4. The method of claim 1 wherein the cells express oct4 and telomerase.

5. The method of claim 1 wherein the cells can differentiate into cell types of at least two of the endodermal, ectodermal, and mesodermal germ layers.

6. The method of claim 1 wherein the cells can differentiate into cell types of endodermal, ectodermal, and mesodermal germ layers.

7. The method of claim 1 wherein the cells express oct4 and telomerase and can differentiate into cell types of at least two of endodermal, ectodermal, and mesodermal germ layers.

8. The method of claim 1 wherein the cells can differentiate into cell types of endodermal, ectodermal, and mesodermal germ layers and express telomerase and oct4.

9. The method of claim 1 wherein the cells are human.

10. The method of claim 1 wherein the cells are derived from bone marrow.

* * * * *

UNITED STATES PATENT AND TRADEMARK OFFICE
CERTIFICATE OF CORRECTION

PATENT NO. : 9,937,208 B2
APPLICATION NO. : 13/150491
DATED : April 10, 2018
INVENTOR(S) : Robert W. Mays Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 8 days.

Signed and Sealed this
Seventeenth Day of September, 2019

Andrei Iancu
*Director of the United States Patent and Trademark Office*